United States Patent [19]
Lai

[11] Patent Number: 6,118,841
[45] Date of Patent: Sep. 12, 2000

[54] DETECTOR ARRAY GEOMETRY FOR HELICAL SCANNING VOLUMETRIC COMPUTED TOMOGRAPHY SYSTEM

[75] Inventor: Ching-Ming Lai, Wakefield, Mass.

[73] Assignee: Analogic Corporation, Peabody, Mass.

[21] Appl. No.: 09/095,554

[22] Filed: Jun. 11, 1998

Related U.S. Application Data

[60] Provisional application No. 60/051,409, Jul. 1, 1997.

[51] Int. Cl.[7] ........................................ A61B 6/03
[52] U.S. Cl. .................... 378/19; 378/4; 378/14; 378/15
[58] Field of Search ................. 378/19, 15, 14; 250/367

[56] References Cited

U.S. PATENT DOCUMENTS

| | | | |
|---|---|---|---|
| 5,291,402 | 3/1994 | Pfoh | 364/413.14 |
| 5,377,250 | 12/1994 | Hu | 378/15 |
| 5,430,785 | 7/1995 | Pfoh et al. | 378/19 |
| 5,510,622 | 4/1996 | Hu et al. | 250/367 |
| 5,583,903 | 12/1996 | Saito et al. | 378/19 |
| 5,668,851 | 9/1997 | Dobbs | 378/19 |
| 5,680,427 | 10/1997 | Dobbs et al. | 378/19 |
| 5,768,331 | 6/1998 | Gordon et al. | 378/19 |
| 5,781,606 | 7/1998 | Dobbs et al. | 378/19 |
| 5,802,134 | 9/1998 | Larson et al. | 378/4 |
| 5,815,546 | 9/1998 | Flohr et al. | 378/19 |
| 5,828,718 | 10/1998 | Ruth et al. | 378/19 |
| 5,848,117 | 12/1998 | Urchuk et al. | 378/19 |
| 5,946,371 | 8/1999 | Lai | 378/19 |
| 5,960,056 | 9/1999 | Lai | 378/4 |

FOREIGN PATENT DOCUMENTS

4224249A1  1/1993  Germany.

OTHER PUBLICATIONS

L.A. Feldkamp, L.C. Davis, and J.W. Kress, "Practical Cone–beam Algorithm," J. Opt. Soc. Am. A, vol. 1, p612, No. 6, Jun. 1984.

D.L. Parker, "Optimal Short Scan Convolution Reconstruction for Fan beam CT," Med. Phys., vol. 9, No. 2, p254, Mar./Apr. 1982.

*Primary Examiner*—David P. Porta
*Assistant Examiner*—Allen C. Ho
*Attorney, Agent, or Firm*—McDermott, Will & Emery

[57] ABSTRACT

In an improved method and apparatus for cone-beam reconstruction, an improved detector array is provided in an asymmetric shape with respect to the translation axis. In a first embodiment, a standard symmetric array is rotated by a tilt angle $\alpha$ about the beam axis. In a second embodiment, the array is formed to have a substantially helical contour. In this manner, efficient use of detector elements is achieved, system pitch is increased, and image quality is enhanced.

28 Claims, 20 Drawing Sheets

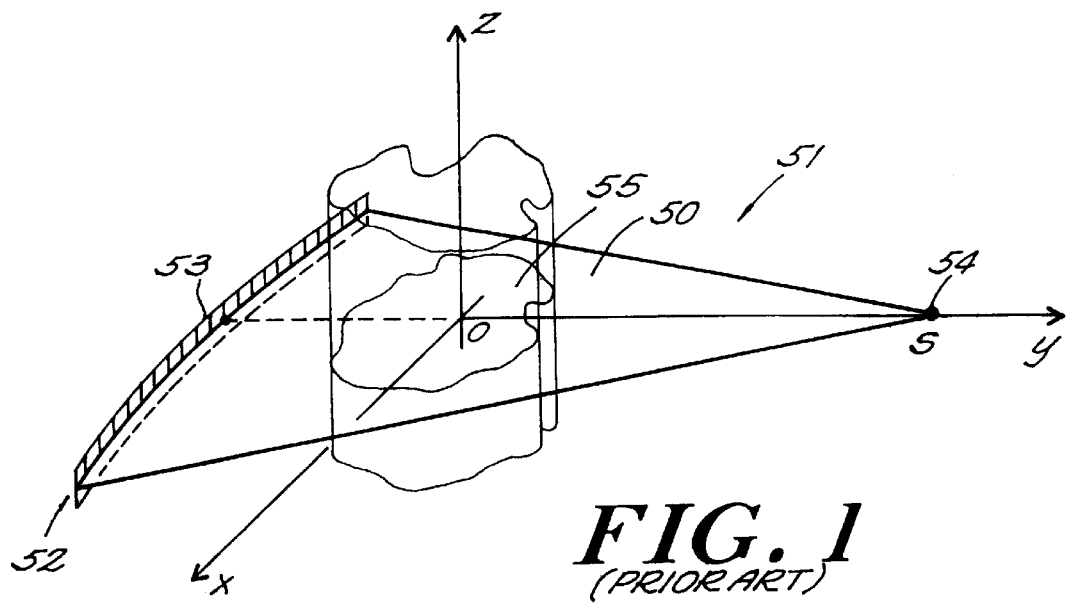
FIG. 1 *(PRIOR ART)*
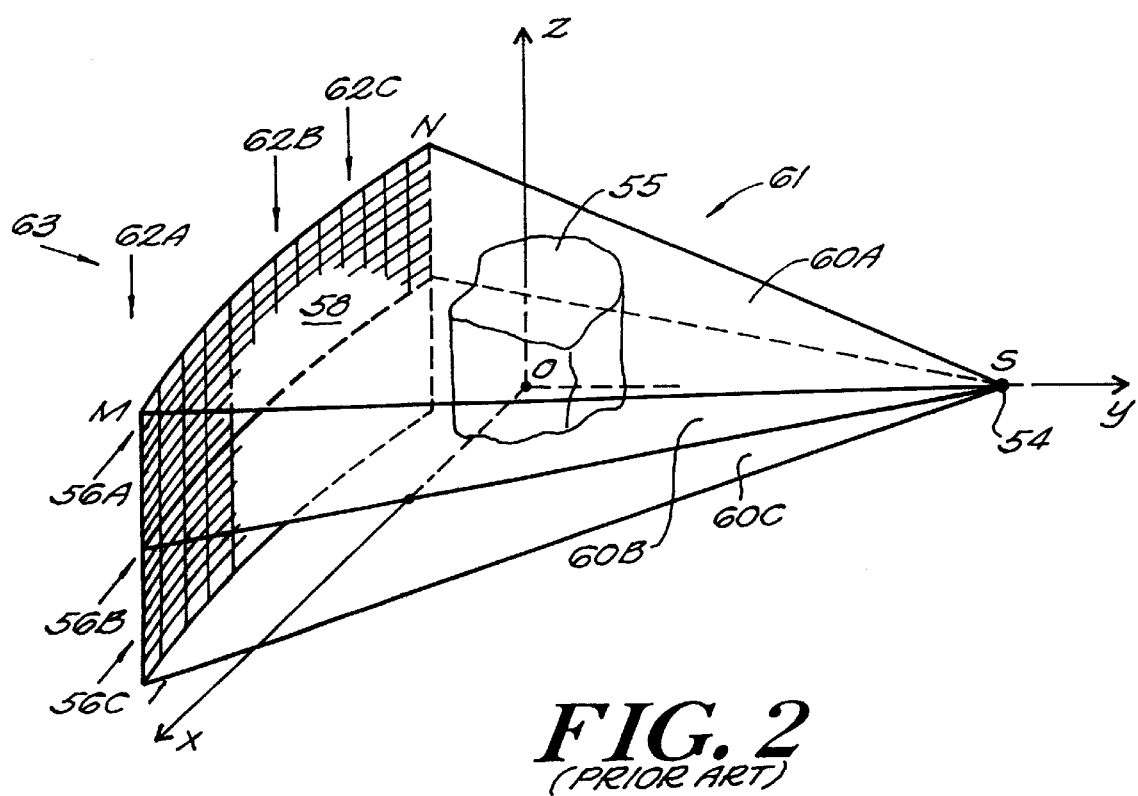
FIG. 2 *(PRIOR ART)*

DETECTOR ARRAY GEOMETRY FOR HELICAL SCANNING VOLUMETRIC COMPUTED TOMOGRAPHY SYSTEM

RELATED APPLICATION

This application claims the benefit of U.S. Provisional Application No. 60/051,409, filed Jul. 1, 1997, the contents of which are incorporated herein by reference.

BACKGROUND OF THE INVENTION

In modem computed tomography (CT) scanner systems, an X-ray source generates an X-ray beam which interrogates an object and is incident on a sensor array. In third-generation CT systems, the source and sensor array are mounted on a gantry which rotates about the object. Successive sets of projections of the object are recorded at incremental gantry rotation angles. After completion of a half rotation of the gantry ("half-scan" system) or a full rotation ("full-scan" system), data from the successive rotation angles are combined in a process known as reconstruction to create a cross-sectional image of the object. In a stationary scan configuration, the object is fixed in position during each scan, while in a translational scan, or "helical" scan, the object and gantry translate relative to one another during a rotational scan, improving system throughput.

In a conventional two-dimensional CT scanner, as shown in Prior Art FIG. 1, the X-ray beam 51 propagates in a planar fan shape 50 between a point source 54 and a sensor array 52 comprising a one-dimensional array of detector elements 53. The fan beam 50 is referred to as a "transaxial fan" because the plane of the fan is perpendicular to the rotation axis, i.e., the z-axis. A two-dimensional image reconstruction process collects the raw data at each rotation angle and following a half-scan, or full-scan, converts the data into a planar pixel image of the portion of the object 55 through which the x-rays have passed. Following each scan, the object may be translated along the z-axis to generate adjacent planar cross-sectional images or "slices" of the object 55 which can be combined to produce a volumetric image.

In a three-dimensional CT scanner, as shown in Prior Art FIG. 2, a conical X-ray beam 61, also referred to as a "cone beam", generated at a point source 54, projects along beam axis y through an object 55 and is incident on a two-dimensional sensor array 63. The array 63 comprises multiple rows 56 (rows 1 . . . M) and multiple columns 62 (columns 1 . . . N of detectors which lie on a cylindrical surface 58. In this configuration, the X-ray cone beam 61 diverges not only along the xy-plane but also diverges along the z-axis.

Each cone beam 61 is composed of multiple layers of transaxial fan beams, three of which are indicated by the numerals 60A, 60B, 60C, each transaxial beam defined between the x-ray point source 54 and one of the rows 1 . . . M of detector elements 56A, 56B, 56C. Note that with the exception of transaxial fan beam 60B, which lies along the xy-plane, the remaining transaxial fan beams, such as beams 60A, 60C, are not perpendicular to the z-axis of rotation, and therefore are not "transaxial" in the strictest sense. Instead, each remaining fan beam, such as either beam 60A, 60C is tilted relative to the xy-plane by a small angle $\beta$, referred to as the "conical angle" as shown in Prior Art FIG. 3. Within this definition, transaxial fan beam 60B, projected along the xy-plane can be envisioned as a transaxial fan beam having a conical angle of 0°.

The x-ray point source 54 and respective columns 1 . . . N of detector elements 62 also define "axial" fan beams, three of which are indicated by numerals 64A, 64B, 64C as illustrated in Prior Art FIG. 4. Each axial fan beam 64 lies on a plane parallel to the rotation axis. With the exception of the fan beam 64B of detector column $j_o$, which lies directly on the yz-plane and therefore projects through the z-axis at all rotation angles, the axial fans of the remaining columns 1 . . . N diverge from the yz-plane by an "axial angle" of $\gamma$. The central axial fan beam 64B, projected along the yz-plane can be envisioned as an axial fan beam having an axial angle $\gamma$ of 0°. While in rotation, a set of line projections are provided at each of a plurality of successive rotation angles of the gantry. The angle of a line projection measured on the xy-plane is referred to as the view angle of the projection. Thus, at rotation angle $\theta$, the line projection within each axial fan beam at axial angle $\gamma$ is associated with the same view angle of $\phi = \theta + \gamma$.

In practice, a conventional two-dimensional reconstruction algorithm is insufficient for reconstructing a three-dimensional volumetric image from cone-beam data collected with a two-dimensional detector array. The three-dimensional cone-beam data cannot be accurately resolved into independent parallel layers along the z-axis for introduction into two-dimensional reconstruction since each transaxial fan beam lies at a conical angle $\beta$ to the z-axis, as described above. Performing two-dimensional reconstruction using this data would therefore result in reconstruction errors for each set of fan beam data, with the exception of the central fan beam 60B along the xy-plane. The reconstruction errors worsen as the conical angle $\beta$ increases. A more accurate three-dimensional reconstruction technique known as cone-beam reconstruction for stationary scan configurations is described in:

1. L. A. Feldkamp, L. C. Davis, and J. W. Kress, "Practical Cone-beam Algorithm", J. Opt. Soc. Am. A, Vol.1, p612, No.6, June 1984.

The foregoing discussion applies to scanning an object which is stationary with respect to the z-axis. In another form of scanning, known in the art as a helical scan, the object and gantry translate relative to one another along a translation axis (typically, the object is translated relative to the gantry), usually parallel to the z-axis, at a constant speed during gantry rotation. From the perspective of the object, the x-ray source and sensors can be envisioned as circling about the object in a helical trajectory during data collection. In a helical scan of a conventional system with single-row detectors, the projection data are first interpolated to the z position of each slice for generating its planar image. These planar images are located contiguously along the z-axis. The contiguous slices can be combined and further processed for various modes of three-dimensional display. Unfortunately, in a cone-beam system, the z-axis translation causes the collected data to deviate further from that data which is required for standard two-dimensional or three-dimensional reconstruction techniques. As a result, the reconstruction errors arising from a helical scan of a cone-beam system are worse than that of a stationary scan. Reconstruction and enhancement methods for cone-beam helical scans are described in:

2. U.S. Pat. No. 5,291,402 issued Mar. 1, 1994, to A. H. Pfoh, "Helical Scanning Computed Tomography Apparatus";

3. U.S. Pat. No. 5,377,250 issued Dec. 27, 1994, to H. Hu,"Reconstruction Method for Helical Scanning Computed Tomography Apparatus with Multi-row Detector Array";

4. U.S. Pat. No. 5,430,783 issued Jul. 4, 1995, to H. Hu, N. J. Pele, and A. H. Pfoh, "Reconstruction Method for Helical Scanning Computed Tomography Apparatus with Multi-row Detector Array Employing Overlapping Beams"; and 5. D. L. Parker, "Optimal Short Scan Convolution Reconstruction for Fan beam CT", Med. Phys., Vol.9, No.2, p254, March/April 1982.

In the foregoing references, data are collected over a full rotation of the gantry, i.e., "full-scan", to reconstruct the volumetric image over the scanned region. However, the image may be reconstructed based on data collected in half rotation of the gantry, i.e., "half-scan". Half-scan imaging offers the advantage of doubling the throughput rate or "pitch" compared to a full-scan, where "pitch" is the extent of object translation along the z-axis during a full rotation of the gantry. In a stationary cone-beam system, the full-scan reconstruction technique provides images generally superior to those of the half-scan reconstruction technique. This is due to the fact that in a full scan, the axial fan beams 66, 68 at view angles φ and φ+π respectively diverge in opposite directions as sketched in Prior Art FIG. 5A, which, when the data is reordered with data from other mutually-opposing views, tends to cancel some of the reconstruction errors. On the other hand, at each view angle φ of a half scan, there is no corresponding fan beam 68 at view angle φ+π which presents an opposite view of the same region of the object.

In a helical scan as shown in Prior Art FIG. 5B, the opposing axial fan beams 66, 68 at view angles φ and φ+π respectively do not correspond to the same z position. As a result, a helical full-scan contains larger reconstruction errors than a stationary full scan. In both full-scan and half-scan cone-beam systems, reconstruction errors increase with increased divergence of the axial X-ray beam. If additional detector rows 56 are used, or if the width of each row increases, reconstruction errors become more severe as the result of increasing the conical angle β.

SUMMARY OF THE INVENTION

The present invention is directed to an improved method and apparatus for cone-beam reconstruction which overcomes the limitations of the prior art. An improved detector array configuration is provided in a more favorable geometry so as to provide for efficient usage of acquired data during cone-beam reconstruction.

In a first aspect, the present invention comprises a computed tomography system for reconstructing a volumetric image of an object including an energy source for irradiating a conical beam centered about a beam axis through the object toward a detector array. The source and the detector array are in rotatable relationship about the object for interrogating the object at successive view angles as the object and beam are translated relative to one another along a translation axis normal to the beam axis. The detector array includes an array of sensor elements arranged in rectangular rows and columns positioned in the path of the beam and rotated above the beam axis by a tilt angle α, where α≠0. In this manner, the columns lie at the tilt angle α, where α≠0 with respect to the translation axis during a scan.

In a preferred embodiment, the tilt angle α is determined as a function of the rate of relative translation of the object, or determined as a function of the rate of rotation of the source and detector array about the object. A preferred embodiment further comprises a mount for mounting the detector array to permit selective adjustment of the tilt angle α. The mount is preferably motor driven for selecting a range of tilt angles α. The detector array may comprise a planar array or may be shaped to lie on a cylindrical surface centered about an axis passing through the source.

In a second aspect, the present invention comprises an improved detector array for use in a computed tomography system for reconstructing a volumetric image of an object. The system includes an energy source for irradiating a conical beam centered about a beam axis through the object toward a detector array. The source and the detector array are in rotatable relationship about the object for interrogating the object at successive view angles as the object and beam are translated relative to one another along the translation axis normal to the beam axis. The improved detector array elements are arranged in rectangular rows and columns. A mount positions the detector array in the path of the beam at a variable tilt angle α about the beam axis such that the columns lie at the tilt angle α with respect to the translation axis during a scan. In a preferred embodiment, the tilt angle α is variable between −5 and +5 degrees.

In a third aspect, the present invention comprises a detector array for use in a computed tomography system for reconstructing a volumetric image of an object. The system includes a source in rotatable relationship with the array about the object for interrogating the object at successive view angles as the object and source are translated relative to one another along the translation axis normal to the plane of rotation. The detector array comprises a two-dimensional array of detector elements arranged in rows and in columns. The detector array is of an asymmetric shape with respect to the translation axis.

In a first preferred embodiment, the detector columns are normal to the detector rows such that the elements are in a rectangular relationship. In this configuration, the detector elements in the top and bottom rows are partially depopulated and/or overpopulated in opposite corners of the array to provide an array having a substantially helical contour.

In a second preferred embodiment, each detector column in the array is shifted along the translation axis by an amount ΔZ with respect to a central column. ΔZ may be determined by the system pitch or by $(j-j_o)*\delta*D*R/(\pi*r)$ where j is the column number, $j_o$ is the central column number, δ is the angular interval between rows, D is the translation distance during a system rotation angle of π, R is the radial distance of the detector array from the X-ray source and r is the radial distance of the center of rotation from the X-ray source.

In a third preferred embodiment, the elements of a subset of the detector columns are elongated along the translation axis with respect to the elements of a central column. The detector elements may be increasingly elongated as the distance to the central column increases.

In each of the above embodiments, the columns and rows of elements of the detector array may lie on a cylindrical surface. Alternatively, the distance between the column and the source may decrease gradually as a function of the position of the column with respect to the central column of the detector array.

The present invention is applicable to a system employing the reconstruction technique referred to as "constant-z interpolation" described in U.S. patent application Ser. No. 09/038,320, "Method and Apparatus for Reconstructing Volumetric Images in a Helical Scanning Computed Tomography System with Multiple Rows of Detectors," filed Mar. 11, 1998, incorporated herein by reference. The present invention is further applicable to the improved reconstruction technique referred to "successive approximation" described in U.S. patent application Ser. No. 09/066,494, "Reconstruction of Volumetric Images by Successive Approximation in Cone-beam Computed Tomography Systems," filed Apr. 24, 1998, incorporated herein by reference.

BRIEF DESCRIPTION OF THE DRAWINGS

The foregoing and other objects, features and advantages of the invention will be apparent from the more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

Prior Art FIG. 1 illustrates an X-ray source and a single row of detectors defining a transaxial fan beam perpendicular to the z-axis of rotation in a prior art conventional computed tomography system.

Prior Art FIG. 2 illustrates an X-ray source and a multiple-row detector array, defining multiple transaxial fan beams and multiple axial fan beams in a prior-art cone-beam tomography system.

Prior Art

Prior Art

Prior Art

Prior Art

DETAILED DESCRIPTION OF PREFERRED EMBODIMENTS

I. Overview

It is well known that in a conventional stationary, single-row detector, half-scan computed tomography system, the transaxial fan beam data required for accurate reconstruction lies within the half-scan rotation angle of $\pi$ plus an additional angle of $2\gamma_{max}$, which is the angular span of the fan beam, as described in Parker, cited above. Without the extra $2\gamma_{max}$ angle, some of the projections are absent and some are redundant (double-sampled) near the starting rotation angle $\theta$ or the finishing rotation angle $\theta+\pi$. The extra $2\gamma_{max}$ scan angle ensures that no projection is absent for reconstruction near the starting and finishing angle. For these double-sampled data, each projection on the left side of the fan at the starting angle $\theta$ is paired with a parallel projection at the right side of the fan at the opposite angle $\phi+\pi$, in which they project along the same path through the object but in opposite directions. The redundancy is compensated by applying proper weighting to average the opposed projections, such that all data are utilized and any discontinuity between the starting and finishing angles is minimized.

This phenomenon is much more complicated for helical scans of a cone-beam system with multiple rows of detectors, where each redundant projection in a pair is collected from a detector in a different row. Although the projections are parallel in xy space, in which the z dimension is disregarded, they have different angles relative to the z-axis because different rows of detectors have different conical angles $\beta$. For this reason, the compensation technique of weighting the redundant projections in a cone-beam system is less effective than in a conventional system with a single row of detectors. Furthermore, unlike a stationary full-scan where the divergence of the X-ray with respect to the scanned object is symmetrical between the first and second half rotations, the cone-beam helical half-scan lacks such symmetry.

The present invention addresses the need for an improved cone-beam reconstruction technique for data collected in a helical half-scan. The novel technique avoids the ill effect of the fan-beam reconstruction algorithm and generates a more accurate three-dimensional image. It also reduces the amount of computations by using parallel-beam backprojection in xy space.

Figure 3:
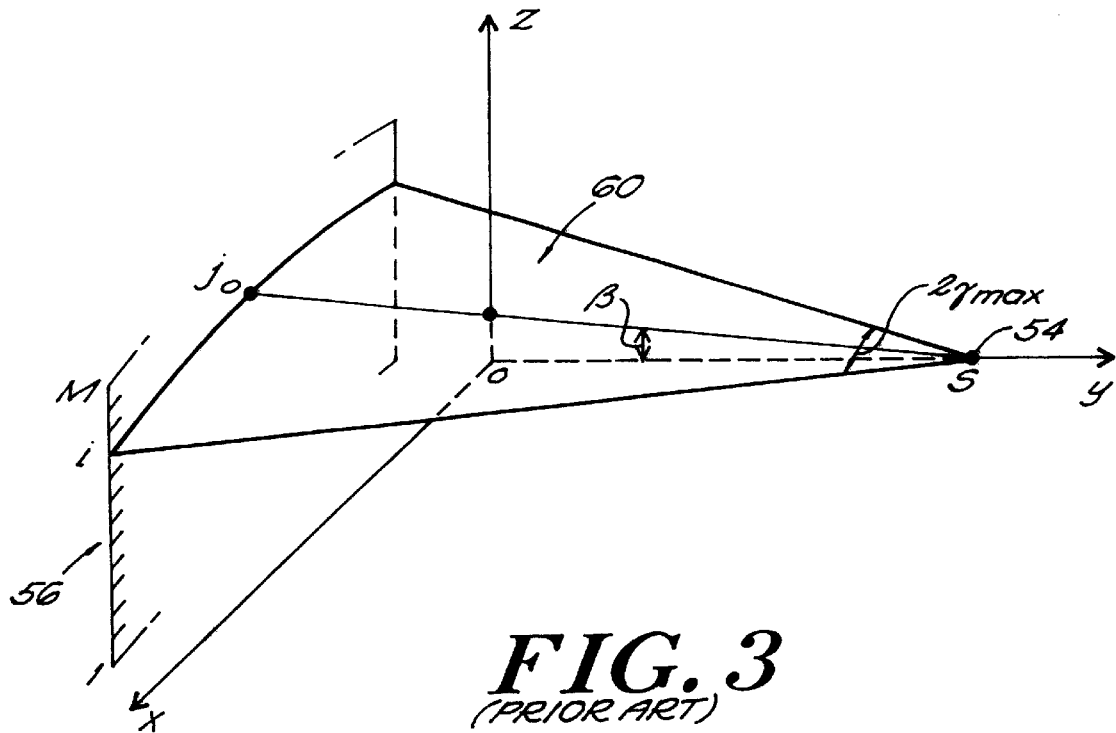
FIG. 3 illustrates the transaxial fan beams of the system of FIG. 2, each directed to a different row of detectors and having a transaxial fan angle of $2\gamma_{max}$ and lying at a conical angle of $\beta$ relative to the xy-plane.
Figure 4:
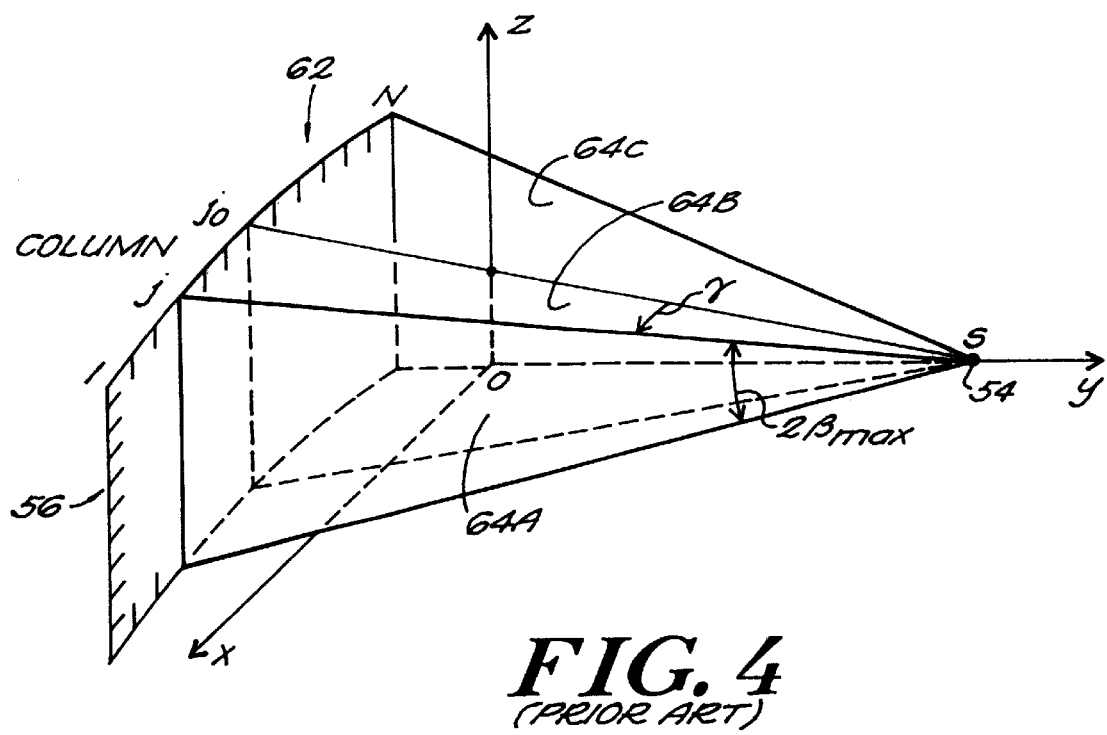
FIG. 4 illustrates the axial fan beams of the system of FIG. 2, each directed to a different column of detectors and having an axial fan angle of $2\beta_{max}$ and lying at an angle of $\beta$ relative to the yz-plane.
Figure 5A:
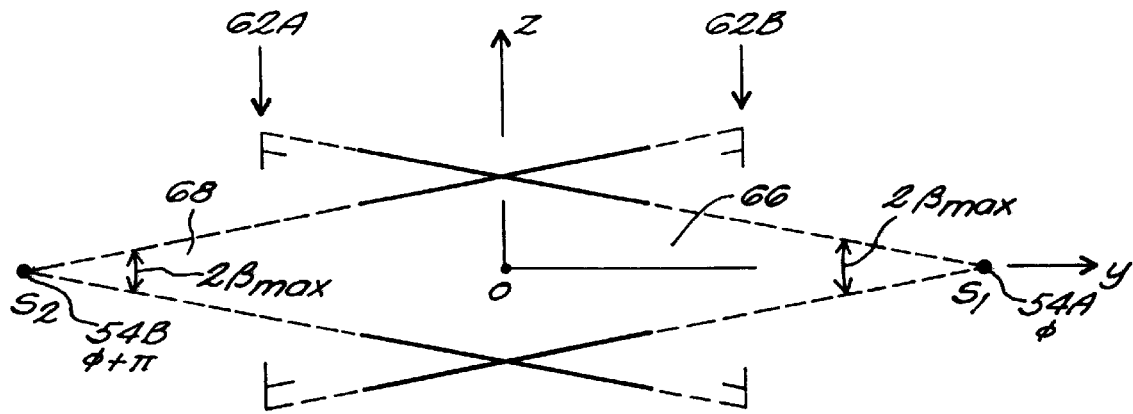
FIG. 5A depicts opposed axial fan beams at view angles $\phi$ and $\phi+\pi$ in a stationary scan.
Figure 5B:
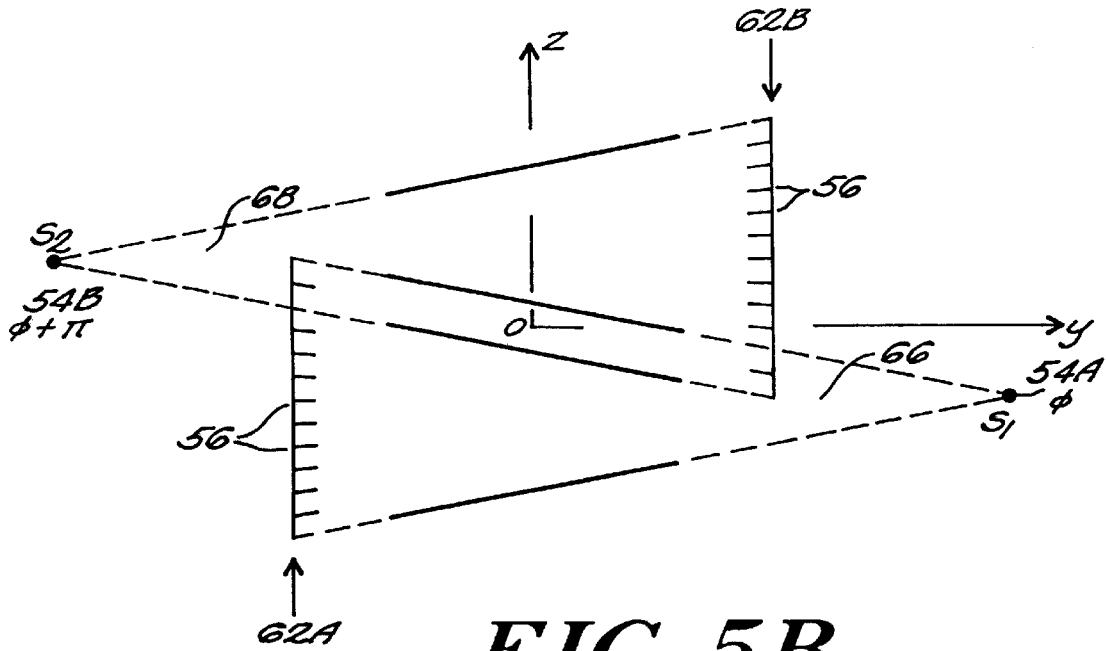
FIG. 5B depicts opposed axial fan beams at view angles $\phi$ and $\phi+\pi$ in a helical scan.
Figure 6:
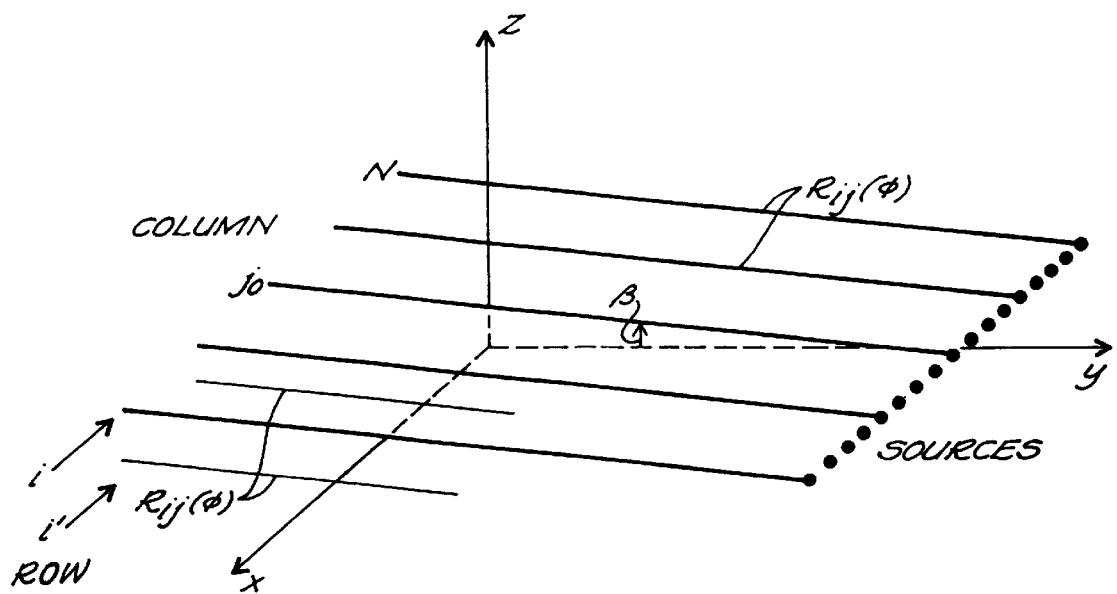
FIG. 6 is an illustration of parallel projections reordered from transaxial fan beam projections, in accordance with the present invention.

In the improved technique of the present invention, the collected data are first converted into projections as a function of the logarithm of the signal intensity sensed at each detector, followed by application of certain corrections for offset, nonlinearity, and other corrections in accordance with well-known computed-tomography techniques. From nearby rotation angles, the fan-beam projections (for each detector row) are reordered into parallel-beam projections $R_{ij}(\phi)$ as illustrated in FIG. 6. At each parallel-beam view angle $\phi$, the reordered projections are parallel to each other in xy space. However, because the projections $R_{ij}(\phi)$ are reordered from different fan-beam rotation angles, the parallel-beam projections within a view angle $\phi$ are at different z positions with respect to the object which translates in the direction of the z-axis, or translation axis. The present invention compensates for this by interpolating projections derived from the same detector column or channel, but different rows of the detector array, to constant-z positions in a process referred to herein as "constant-z interpolation".

The constant-z interpolated parallel-beam projections are sampled at equal angular intervals for each row. To prepare for filtered backprojection, projections from each detector row are interpolated into equal spatial intervals. The equally-spaced projections are then filtered by a convolution kernel for each detector row in a manner similar to the convolution for reconstructing a two-dimensional image from parallel-beam projections.

In the final stage of reconstruction, the convolved parallel-beam projections are backprojected using three-dimensional backprojection techniques. In the preferred configuration, for each value of $\phi$, all rows of projections at parallel-beam view angles $\phi$ and $\phi+\pi$ are grouped together to backproject for those voxels scanned. Each voxel is backprojected from the convolved projection which passes through the voxel either at view angle $\phi$ or $\phi+\pi$. Since the voxel is not precisely located at the path of a projection, the value for backprojection to a voxel is interpolated from adjacent projections.

In the description to follow, assume conical beams are emitted from a point source to a two-dimensional array of detectors. Assume also that the detector array lies on a cylindrical surface centered about an axis which passes through the source, and that the detector columns lie parallel to the rotation axis, or z-axis, and perpendicular to the xy-plane. The present invention is equally applicable to other conceivable helical scanning geometries, however, for purposes of the following illustration, the foregoing assumptions apply. Note that for purposes of the present invention, the term "channel" refers to a detector element in a given row of detectors, while the term "column" refers to an arrangement of a column of channels (or elements) in adjacent detector rows, i.e., parallel to the rotation axis.

II. Reordering of Projections From Fan to Parallel Beams

The initial step of reordering the fan beam projections collected from each row of detectors into parallel-beam projections independent of other rows will now be described in detail with reference to the various drawings. Assuming that $P_{ij}(\theta)$ represents the amplitude of a line projection derived from a detector located in the jth column and ith row at fan-beam rotation angle $\theta$, and $R_{ij}(\phi)$ represents the reordered projection amplitude in the jth column of ith row at parallel-beam view angle $\phi$, then $$R_{ij}(\phi)=P_{ij}(\phi-(j-j_o)*\delta) \tag{1}$$

where $\delta$ represents the angular spacing between adjacent columns and $j_o$ represents the central column. If the detector array has M rows with N columns or detector channels per row, then $$i=1, 2, \ldots, M$$
$$j=1, 2, \ldots, N$$
$$j_o=(N+1)/2 \tag{2}$$

assuming the detector array 63 (see FIG. 7) is symmetrical about the rotation axis. Since the fan angle of the transaxial fan is $2\gamma_{max}$, the angular spacing $\delta$ is related to the fan angle by:

$$\delta=2\gamma_{max}/(N-1). \tag{3}$$

During a scan, the gantry rotates about the z-axis and the data are collected at successive intervals of the gantry rotation angle:

$$\theta=\theta_k=k*\Delta\theta \tag{4}$$

where k is an integer and $\Delta\theta$ is the increment of the gantry rotation angle between successive fan beam projections.

Assuming that the parallel-beam view angle $\phi$ is chosen to have the same rotation angle increment $\Delta\theta$, as preferred, then $\phi=\phi_m=m*\Delta\theta$, with integer m=0, 1, 2, . . . . If the data are acquired at such a rate that the incremental rotation angle is equivalent to the angular spacing between columns, or $\Delta\theta=\delta$, then Equation 1 becomes $$R_{ij}(\phi)=P_{ij}((m+j_o-j)*\Delta\theta)=P_{ij}(\theta_k)$$

with $k=m+j_o-j$ \hfill (5)

In Equation 5, because $(m+j_o-j)$ is an integer, the reordered projection $R_{ij}(\phi)$ can be obtained from $P_{ij}(\theta_k)$ at successive fan-beam rotation angles.

In the case where the incremental rotation angle between successive fan beam projections is greater than the angular column spacing, i.e., $\Delta\theta>\delta$, or $\Delta\theta>a*\delta$, with a>1. Equation 1 becomes $$R_{ij}(\phi)=P_{ij}((m+(j_o-j)/a)*\Delta\theta)=P_{ij}(\theta_{ka}),$$

$k_a=m+(j_o-j)/a$ \hfill (6)

In this case, $k_a$ is not an integer unless $(j_o-j)$ is divisible by a.

Let $k\leq k_a\leq k+1$, where k is the truncated integer of $k_a$ with a remainder of $f=k_a-k$. This gives $\theta_{ka}=\theta_k+f*\Delta\theta$ with $0\leq f<1$ \hfill (7)

Combining Equations 6 and 7, the reordered projections $R_{ij}(\phi)$ can be calculated as $$R_{ij}(\phi)=(1.0-f)*P_{ij}(\theta_k)+f*P_{ij}(\theta_{k+1}) \hfill (8)$$

if linear interpolation is used. Therefore, Equation 8 applies to the derivation of reordered projections $R_{ij}(\phi)$ in a system where the incremental rotation angle is greater than the angular column spacing, or $\Delta\theta>\delta$, while Equation 5 applies where they are equal, $\Delta\theta=\delta$ III. Constant-z Interpolation The resulting reordered projections $R_{ij}(\phi)$ illustrated in FIG. 6 for all channels j at a view angle $\phi$ are parallel to each other because they are derived from detectors of the same row i. However, they are not parallel to reordered projections $R_{ij}(\phi)$ from other rows i', because of the difference in conic angle between rows i and i'. Moreover, the location of each reordered projection along the z-axis is column-dependent because, in a helical scan, each projection is reordered from a fan beam of the same detector at a different z position. Accurate convolution, later performed as a precursor to the backprojection process, requires that the reordered projections lie on or nearly on the plane of the slice selected for convolution. For this reason, the reordered projections $R_{ij}(\phi)$ of row i, parallel in the xy space, but considerably separated in z-position, are interpolated or, in other words, re-sampled, to a set of projections still parallel in xy space but at the constant z-position of the reconstructing slice.

In the next step of the present invention, in a process referred to as constant-z interpolation, the reordered projections $R_{ij}(\phi)$ within the same column are used to generate projections at a constant z-position, and therefore suitable for convolution. Following constant-z interpolation, the interpolated reordered projections of all columns, even though they are not exactly perpendicular to the z-axis (i.e., their cone angles vary), are made to closely correspond to a constant z-position for each interpolated row i at each view angle $\phi$.

With the exception of the projection path corresponding to the central row of detectors $i_o$, no projection paths are exactly perpendicular to the z-axis. Therefore, the z-coordinate of each projection varies along its path between the source and detector element. A reference point referred to as the "midpoint" of the projection path is selected to represent the z-position of the projection. The "midpoint" is defined as the point of intersection between the projection path and a plane passing the z-axis and normal to the projection path (or, more precisely, a plane passing through the z-axis and normal to the axial fan containing the projection). Note that the midpoint of a projection line is not necessarily halfway between the source and detectors, nor does it necessarily correspond with the rotation axis. The z-coordinate of the midpoint defines the z-position of the projection path. The midpoints of projections of the same axial fan, i.e, the same column, lie along a line parallel to the z-axis, while midpoints of projections derived from the same transaxial fan, i.e., the same row, lie on a curve slightly deviated from a circular arc.

Figure 7:
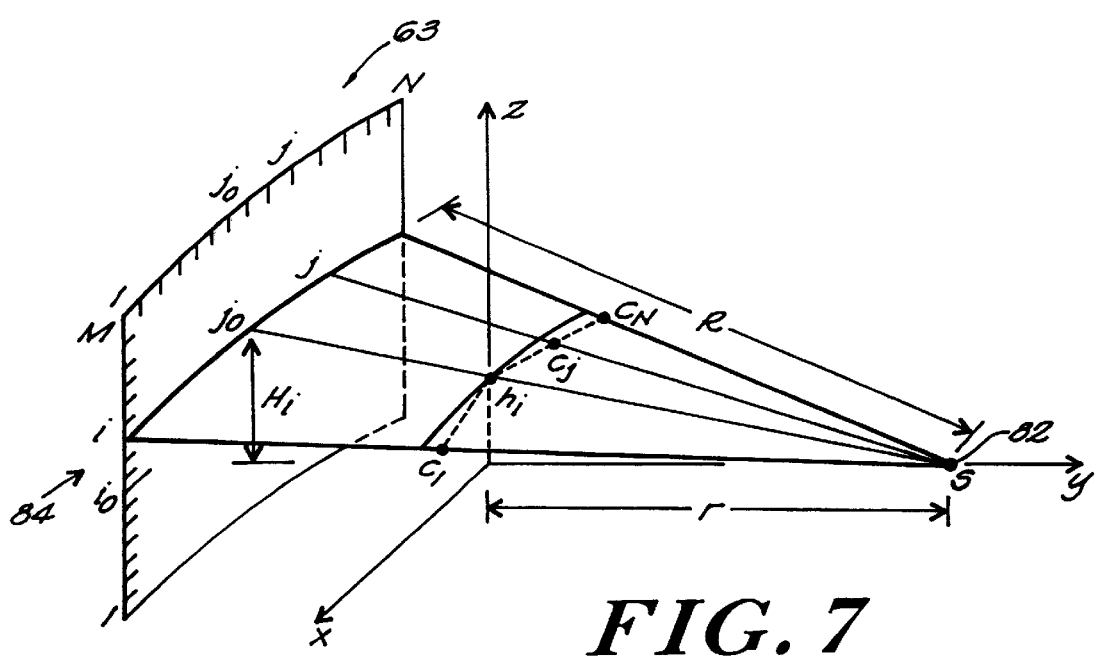
FIG. 7 is an illustration of the geometry of a transaxial fan beam and the midpoints of corresponding projection paths in accordance with the present invention.
Figure 8:
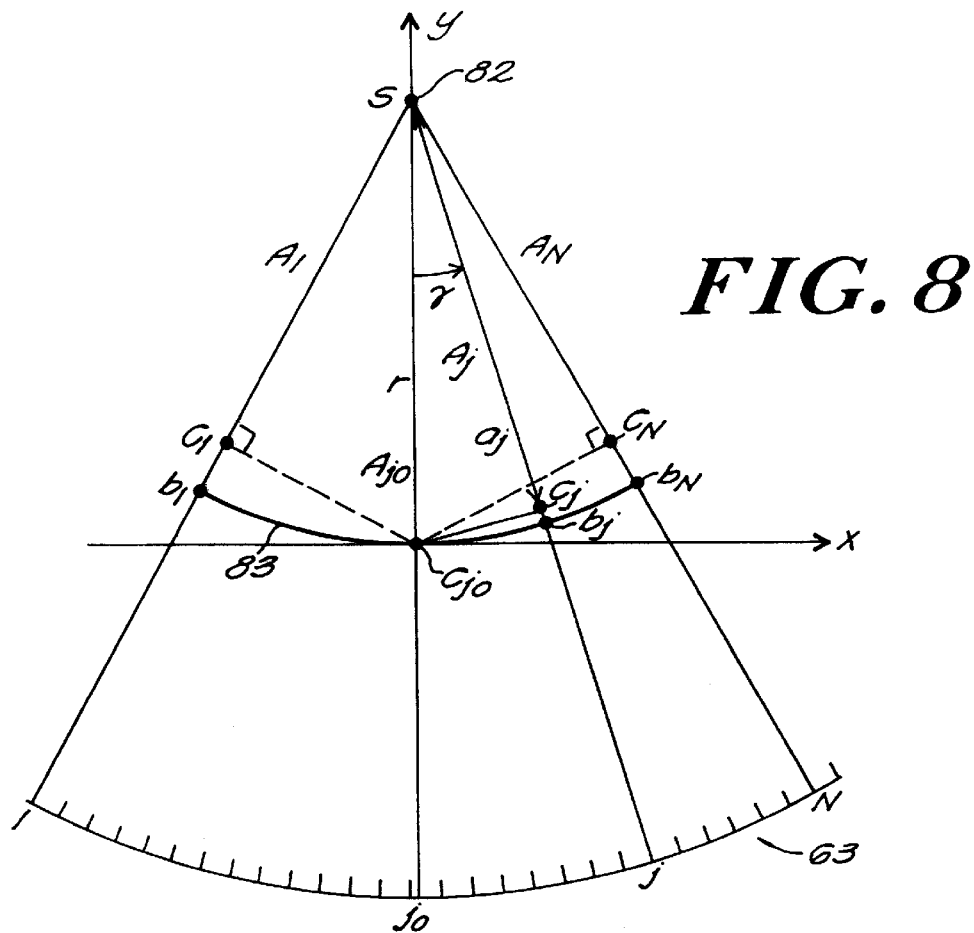
FIG. 8 is a top view of the illustration of midpoints of the projection paths of FIG. 7 in accordance with the present invention.

The loci of the midpoints on a transaxial fan are shown in FIG. 7, and marked as $c_1 \ldots c_N$ corresponding to detector channels 1 . . . N in detector row 84. A top view of the midpoints $c_1 \ldots c_N$ is illustrated in FIG. 8, where a projection path such as $A_j$ is derived from the central row of detectors of the axial fan perpendicular to the xy plane. Using detector column j as an example, $c_j$ is the midpoint of the projection path $A_j$, and $b_j$ lies on the circular arc 83 which is centered about the X-ray source and passing the z-axis. For the projection $A_{jo}$ of the central detector column $j_o$, midpoint $c_{jo}$ intersects the circular arc 83 and coincides with the center of rotation O. For other detector channels, the distance $a_j$ from the X-ray source 82 to the midpoint $c_j$ is slightly shorter than the radius r of the circular arc 83. The distance $a_j$ can be represented as:

$$a_j=r*\cos(\gamma)=r*\cos((j-j_o)*\delta) \hfill (9)$$

where $j_o$ is central detector column number, and $\delta$ represents the angular spacing, as defined earlier.

Figure 9:
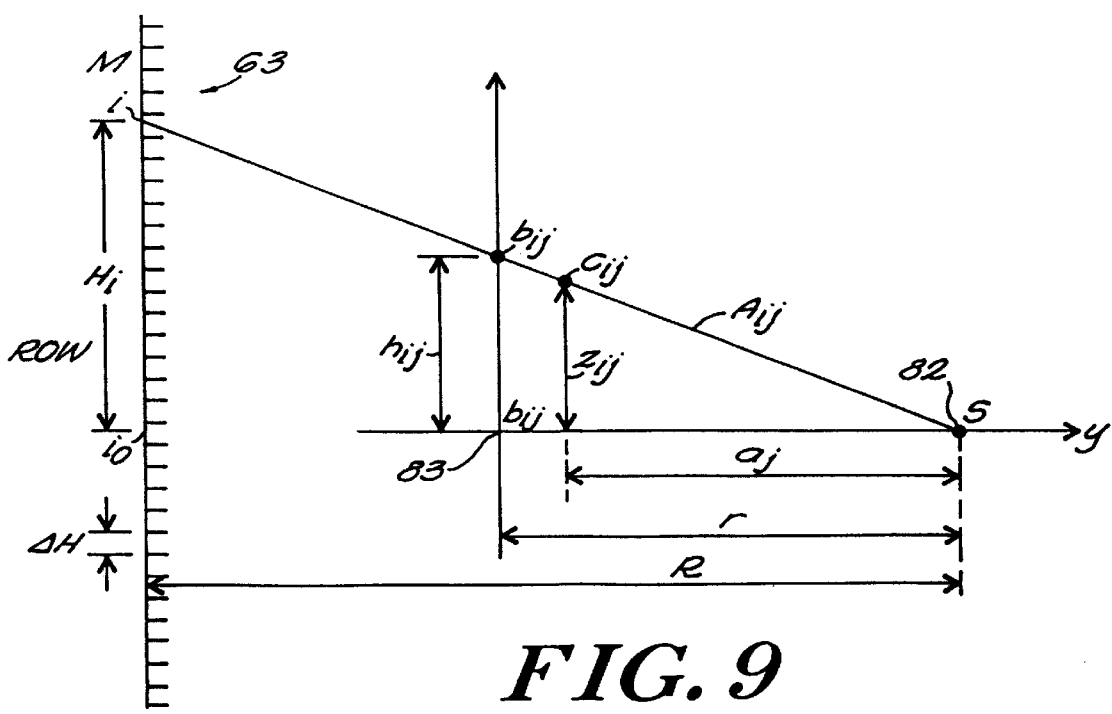
FIG. 9 is a side view of the illustration of the loci of midpoints of the projection paths of FIG. 7 in accordance with the present invention.

The loci of midpoints from the jth axial fan are illustrated in FIG. 9 on the yz plane. The midpoint $c_{ij}$ of a projection path $A_{ij}$ and its corresponding z-coordinate $z_{ij}$ are shown, with the index i indicating the projection of the ith detector row of rows 1 . . . M. The point corresponding to $b_j$ of FIG. 8 is denoted as $b_{ij}$, and its z-coordinate is $h_{ij}$. Assuming a cylindrical detector array 63 centered about the X-ray source, the radial distance of the detector array 63 and the radial distance of the center of rotation O from the X-ray source are referred to as R and r respectively. Assuming the z-axis position of the ith detector row is $H_i$, then the z-coordinate of point $b_{ij}$ in FIG. 9 can be calculated as $$h_{ij}=H_i*r/R=h_i \hfill (10)$$

which is the same for all detector channels within the same row; therefore the index j can be omitted. If the spatial interval between adjacent detector rows is represented by $\Delta H$, then the z-coordinate increment of $h_{ij}$ between successive rows is:

$$\Delta h=\Delta H*r/R. \hfill (11)$$

The z-coordinate $h_{ij}$ of point $b_{ij}$ can therefore be expressed as $$h_{ij}=h_i=(i-i_o)*\Delta h \hfill (12)$$

where $i_o$ is the central row number.

From the geometry of FIG. 9, the z-coordinate $z_{ij}$ of the midpoint $c_{ij}$ can be calculated as a proportion of the distance $a_j$ to the radius r, relative to $h_{ij}$:

$$z_{ij} = h_{ij} * a_j/r. \quad (13)$$

Assuming that the object translates for a distance D during a gantry rotation angle of π, equivalent to a pitch of 2D for a helical scan, the z-position of the fan beam projection $P_{ij}$ (θ) is:

$$z_{ij}(\theta) = z_{ij} + \theta * D/\pi, \quad (14)$$

where θ represents the rotation angle.

Combining Equations 12 through 14:

$$z_{ij}(\theta) = (i - i_o) * \Delta h * a_j/r + \theta * D/\pi \quad (15)$$

Using the relation $\theta = \phi - (j - j_o) * \delta$ in Equation 1, the z-position $z_{ij}(\phi)$ for the reordered parallel-beam projection $R_{ij}(\phi)$ can be written as:

$$z_{ij}(\phi) = (i - i_o) * \Delta h * a_j/r + (\phi - (j - j_o) * \delta) * D/\pi \quad (16)$$

With the z-position given in the above Equation 16 for each projection path, the reordered projections $R_{ij}(\phi)$ can be interpolated from adjacent rows along the z-direction, such that the interpolated projections $S_{ij}(\phi)$ have a constant z-position for each row. Assume the constant z-position is chosen to be equal to the z-position of the central column $j_o$:

$$z_{ij0}(\phi) = (i - i_o) * \Delta h + \phi * D/\pi, \quad (17)$$

where, for the central column $j_o$, $a_j = a_{j0} = r$ and $j = j_o$.

If i' is the corresponding row number in column j with this z-position, then combining Equations 16 and 17:

$$(i' - i_o) * \Delta h * a_j/r + (\phi - (j - j_o) * \delta) * D/\pi = (i - i_o) * \Delta h + \phi * D/\pi$$

or, $$i' = i + (j - j_o) * \delta * D * r/(66\ h * a_j * \pi). \quad (18)$$

with $a_j$ given by Equation 9. Note that Equation 18 is independent of the parallel-beam angle φ, and therefore the projections will be interpolated in exactly the same manner for every view angle.

In general, i' is not an integer. Let k be the truncated integer of i', that is $$i' = k + f_k \quad (19)$$

with $0 f_k < 1.0$. If linear interpolation is employed, the constant-z interpolated projections $S_{ij}(\phi)$ can be calculated from two adjacent rows k and k+1 of the reordered projections as $$S_{ij}(\phi) = (1.0 - f_k) * R_{kj}(\phi) + f_k * R_{k+1,j}(\phi) \quad (20)$$

Higher-order interpolation methods are preferred to calculate for $S_{ij}(\phi)$, to obtain more accurate results.

Figure 10A:
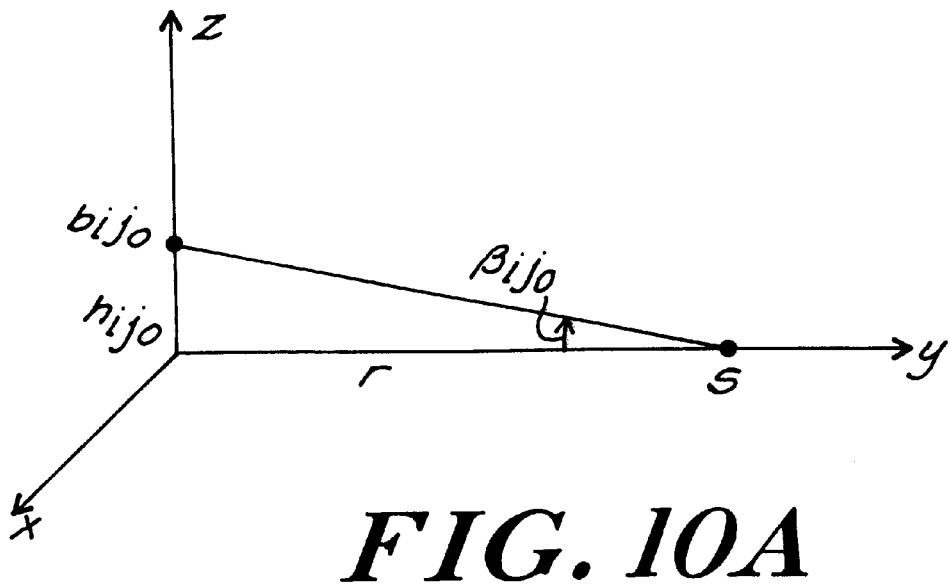
FIG. 10A is an illustration of the conical angle of the central detector column $j_o$ in accordance with the present invention.
Figure 10B:
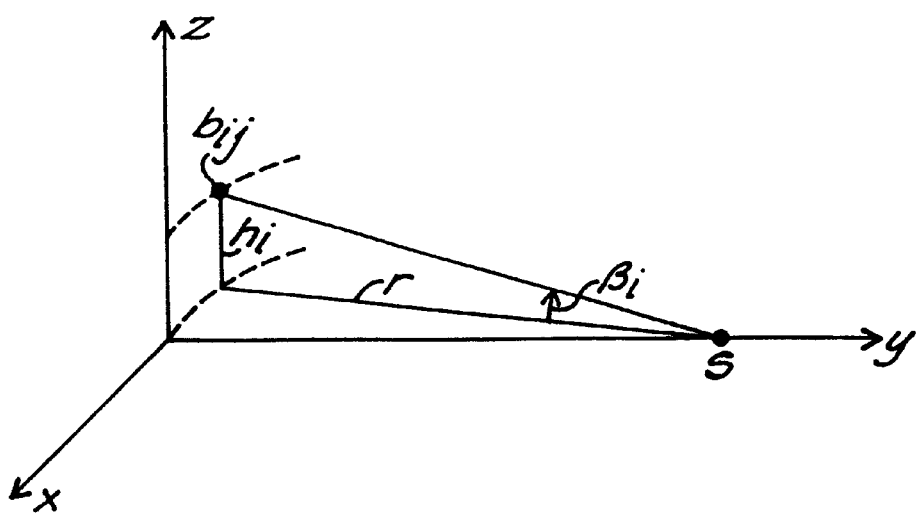
FIG. 10B is an illustration of the conical angle of the jth column of detectors in accordance with the present invention.

Although each row of constant-z interpolated projections $S_{ij}(\phi)$ represents parallel-beam projections in xy space at a constant-z position, they are not truly parallel in three-dimensional space as each projection has a different conical angle β, referring to the angle β between the projection path and the xy-plane. The conical angle for each projection $S_{ij}$ (φ) can be found by returning to the original geometry as shown in FIGS. 10A and 10B which illustrate the conical angle $\beta_{ij}$ for the central detector column $j_o$ and the jth detector column respectively of detector row i.

In terms of $h_i$ and r:

$$\beta_i = \tan^{-1}(h_i/r). \quad (21)$$

The conical angle $\beta_i$ is the same for all channels of the original fan-beam projections $P_{ij}$ within the same transaxial fan, because $h_{ij} = h_{ij0} = h_i$.

Since each row of the reordered parallel-beam projections $R_{ij}$ is reordered from the same row of fan beam projections $P_{ij}$ at different rotation angles θ, they each have the same conical angle $\beta_i$. Combining Equations 12 and 21 gives:

$$\beta_i = \tan^{-1}((i - i_o) * \Delta h/r) \quad (22)$$

Since the constant-z interpolated projections $S_{ij}(\phi)$ are interpolated from the parallel-beam projections $R_{i'j}(\phi)$, with i' depending on the channel j, the conical angle $\beta_{ij}$ of $S_{ij}(\phi)$ varies with the row number i as well as the column number j. For the jth column in the ith row, the conical angle of $S_{ij}(\phi)$ is $$\beta_{ij} = \tan^{-1}((i' - i_o) * \Delta h/r)$$

Substituting i' from Equation 18, the conical angle becomes $$\beta_{ij} = \tan^{-1}((i - i_o) * \Delta h/r + (j - j_o) * \delta * D/(a_j * \pi)) \quad (23)$$

If the conical angles $\beta_{ij}$ were zero for all detectors in all rows, reconstruction would be as accurate as in the conventional system. The non-vanishing conical angles $\beta_{ij}$ introduce reconstruction errors to the image. However, it does not make much difference in the extent of the reconstruction errors whether the conical angles are equal in the same row or if they vary gradually from channel to channel as in Equation 23, providing the magnitudes of the conical angles are in the same range. The reconstruction errors are mainly determined by the magnitude of deviation of the projection path from the reconstructing slice plane, regardless of whether the deviation occurs within the same view or different views.

Figure 11:
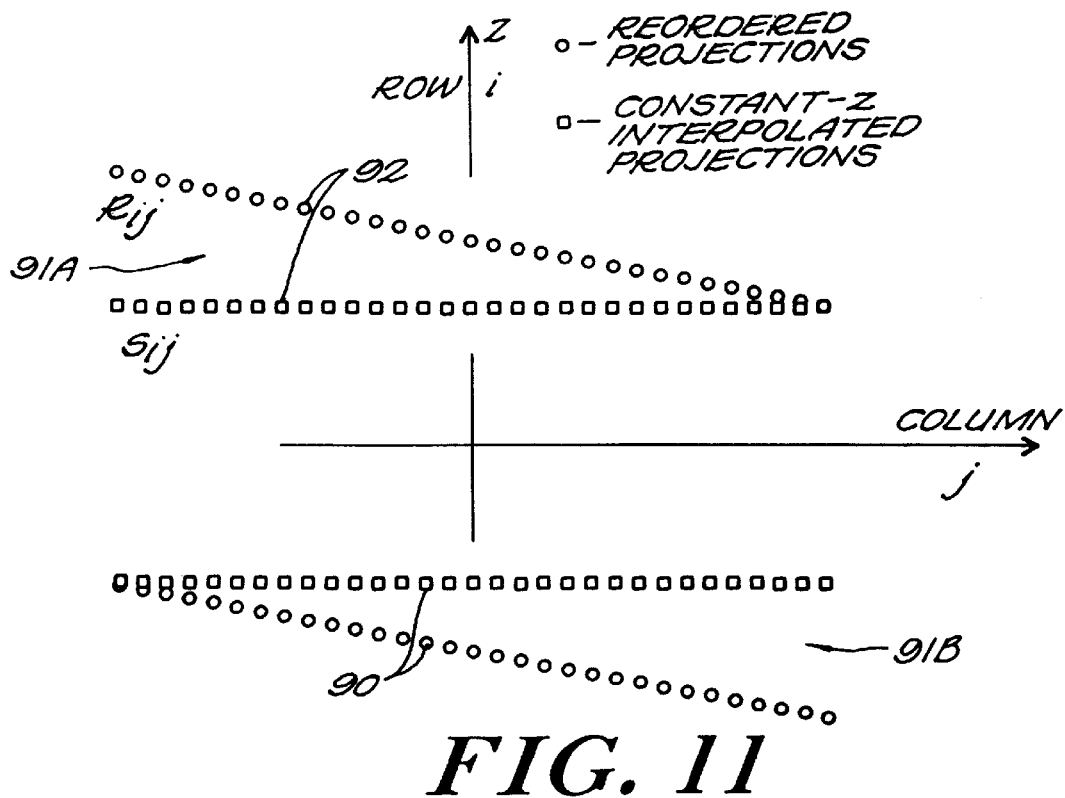
FIG. 11 is an illustration of the z positions of the first- and last-row projection data prior to and following constant-z interpolation in accordance with the present invention.

Since the constant-z interpolated projections $S_{ij}$ are interpolated from the reordered projections $R_{ij}$, the interpolated projections $S_{ij}$ have a smaller positional range in z dimension than the reordered projections $R_{ij}$. FIG. 11 is a plot of the z-positions of the first row 90 and last row 92 of $R_{ij}$ and $S_{ij}$ at a view angle φ. To have valid interpolated projections $S_{ij}$ for all columns, the number of rows for the constant-z interpolated projections $S_{ij}$ must be smaller than that of the reordered projections $R_{ij}$, assuming the same spacing between adjacent rows. If the original number of rows for $R_{ij}$ is M, and the reduced number of rows for $S_{ij}$ is m, the longest translation distance D for either a full-scan or a half-scan will be $$D = m * \Delta h \quad (24)$$

where m<M. Thus, to ensure all interpolated constant-z projections $S_{ij}$ are within the scanning range, the maximum pitch is preferably D, as given in Equation 24 for a full-scan system, and 2D for a half-scan system.

IV. Interpolation for equal spatial intervals

Interpolated constant-z projections $S_{ij}(\phi)$ are derived from original projections which are separated by a constant angular interval δ in the tansaxial fan, as given in Equation 3 for a cylindrical detector array. Although the original projections have been reordered into parallel projections $R_{ij}$ in xy space, the spatial intervals between adjacent projections are unequal, contrary to preferred parallel-beam reconstruction techniques where the spacings should be equal. It is therefore preferable to interpolate the constant-z interpolated projections $S_{ij}(\phi)$ a second time, such that the resulting equal-spaced projections $T_{ij}(\phi)$ have an equal spatial interval d for every row.

Figure 12:
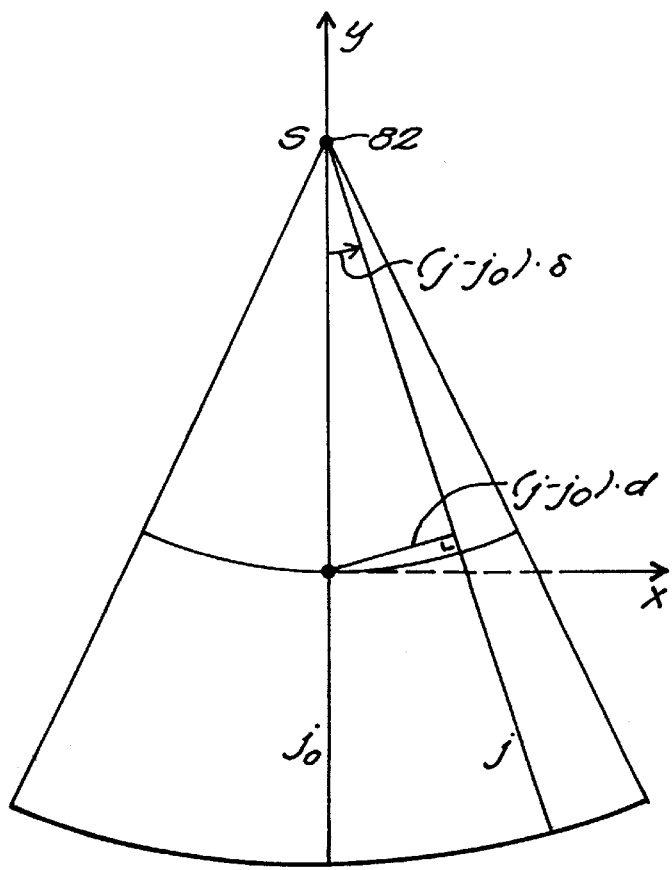
FIG. 12 illustrates the spatial distance and angular distance of a projection path from the central projection, in accordance with the present invention.

To interpolate for detector column j of the equal spaced projections $T_{ij}(\phi)$, the corresponding column j' in the interpolated constant-z projections $S_{ij'}(\phi)$ can be calculated from the following relationship:

$$(j-j_o)*d = r*\sin((j'-j_o)*\delta) \tag{25}$$

where $j_o$ is the central column shown in FIG. 12. Rearranging Equation 25, gives:

$$j' = j_o + \sin^{-1}((j-j_o)*d/r)/\delta. \tag{26}$$

It is preferable to use the spacing between the central column and its adjacent channel, that is the spatial interval between the projections $S_{ij0}(\phi)$ and $S_{i,j+1}(\phi)$, as the constant d.

Based on Equation 26, equal-spaced projections $T_{ij}(\phi)$ are interpolated from the interpolated constant-z projections $S_{ij}(\phi)$ for each row i at each view angle $\phi$. High order interpolations are preferred for this calculation, for example the well-known four-point or six-point Everett interpolation.

V. Convolution

The next step in the inventive technique is the convolution of the equal-spaced projections $T_{ij}(\phi)$. Just like the two-dimensional reconstruction in a conventional scanner of single-row detector system, the equal-spaced projections $T_{ij}(6)$ are oversampled in the low-frequency components from different view angles. For example, the DC component of $T_{ij}(\phi)$ represents the sum of all projections in the ith row, which is the total mass of the object being illuminated by the X-ray beams of the ith row. If the conical angles $\beta_{ij}$ are zero as in the two-dimensional reconstruction case, the DC component of $T_{ij}(\phi)$ in each row would be the same for all view angles $\phi$. The other low-frequency components are not as redundant as the DC component, but nevertheless they are oversampled. The convolution operates as a high-pass filter which de-emphasizes the low-frequency components to equalize the sampling in the two-dimensional frequency space for backprojection.

The original projections do not illuminate the same plane of the object as the view angle changes due to non-vanishing conical angles $\beta_{ij}$ and the translation along the z-axis. But for projections $T_{ij}(\phi)$, which have been interpolated to a constant-z-position, the projections are only slightly deviated from the xy plane at that z-position if the conical angles $\beta_{ij}$ are small. In other words, for small conical angles, the sampling in two-dimensional frequency space approximates the case of a zero conical angle. For small conical angles, it is a good approximation to use the same convolution kernel as a conventional two-dimensional parallel-beam reconstruction.

In view of this, in a preferred embodiment of the present invention, the equalspaced projections $T_{ij}(\phi)$ are filtered with a conventional convolution kernel to provide filtered projections $U_{ij}(\phi)$ for each row i at each view angle $\phi$. The filtered projections $U_{ij}(\phi)$ are later used for backprojection.

To appreciate the effects of convolution, consider a backprojected point spread function without convolution. If the intensity data of the sensed object is negligible everywhere except at a single point, the image intensity resulting from the backprojection will peak at this point, and distribute to surrounding regions. The high-pass convolution kernel applied to the projections sharpen this point spread function. The filtering kernel is preferably a narrow sinc function in the spatial domain. Its amplitude peaks at the center and drops off rapidly toward both sides. Therefore, it is important to keep the nearby projections on the same plane for the filtering kernel to work properly. However, those projections at a location far from the center point can be slightly deviated from the plane, since they do not have much response to the high-pass filtering kernel.

VI Three-Dimensional Backprojection

A. Overview

Following convolution, the filtered projections $U_{ij}(\phi)$ are backprojected along their corresponding X-ray beam paths to form a three-dimensional volumetric image. Due to the conical angle $\beta_{ij}$, each voxel is, in general, backprojected from different rows of filtered projections $U_{ij}(\phi)$ at different view angles $\phi$. Since a voxel does not lie exactly on the projection path of a detector, the data for backprojecting to the voxel should be interpolated from the filtered projections $U_{ij}(\phi)$ of adjacent columns and adjacent rows. Furthermore, in a helical scan, successive sections of the object along the z-direction are continuously scanned. The data is grouped and processed in a certain sequence, such that the volumetric images can be reconstructed section-by-section in a continuous and orderly manner.

Consider a coordinate system xyz which rotates with the gantry, but translates with the object. It is the equivalent to envision that under this coordinate system the object is rotating about the z-axis and the gantry is translating along the z direction. The axial projection paths of the central column $j_o$ are plotted on the yz plane in FIGS. 13A, 13B, 13C under this coordinate system. The axial fans of other columns j also lie along yz planes but at different x positions.

Figure 13C:
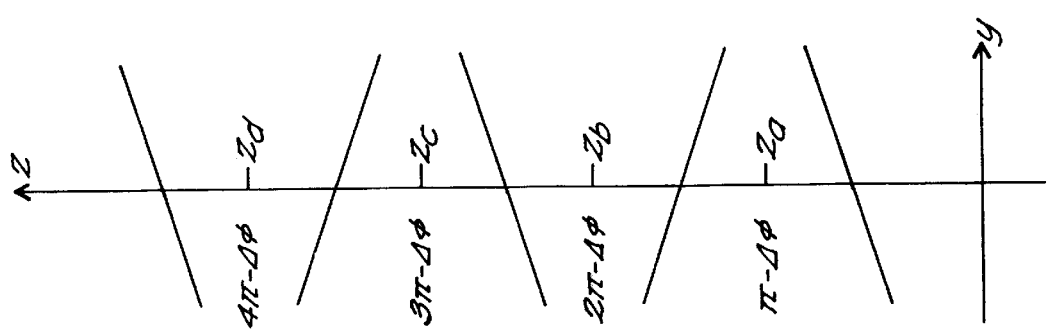
FIGS. 13A, 13B and 13C illustrate axial projections from a plurality of view angles, translated with respect to the z-axis in accordance with the present invention.
Figure 13B:
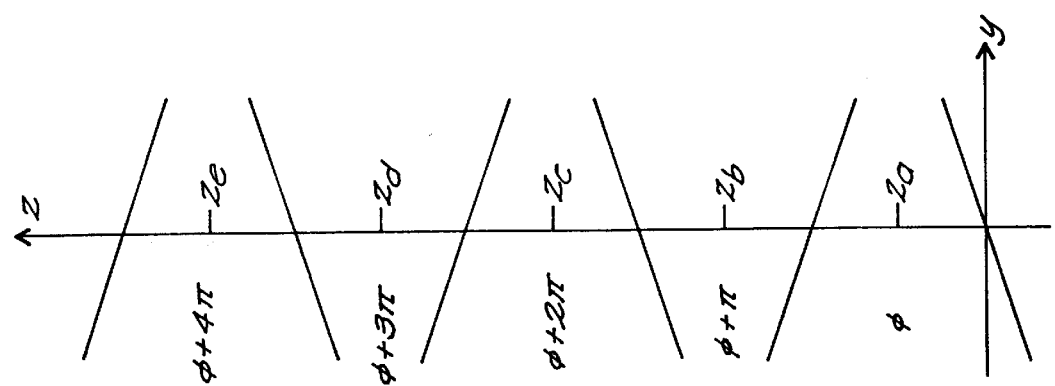

In FIG. 13B, the projection paths from view angles $\phi$, $\phi+\pi$, $\phi+2\pi$, $\phi+3\pi$ are superimposed. The projection data for these four view angles were acquired at every half rotation when the gantry center is at the z-position of $z_a$, $z_b$, $z_c$, and $z_d$. These z-positions are separated by a constant distance D, equal to half of the pitch, or half the translation distance per rotation of the system. Because of the half-rotation difference, the paths for the view angles $\phi$ and $\phi+2\pi$ are plotted in the reverse y-axis direction with respect to the view angles $\phi+\pi$ and $\phi+3\pi$.

Figure 13A:
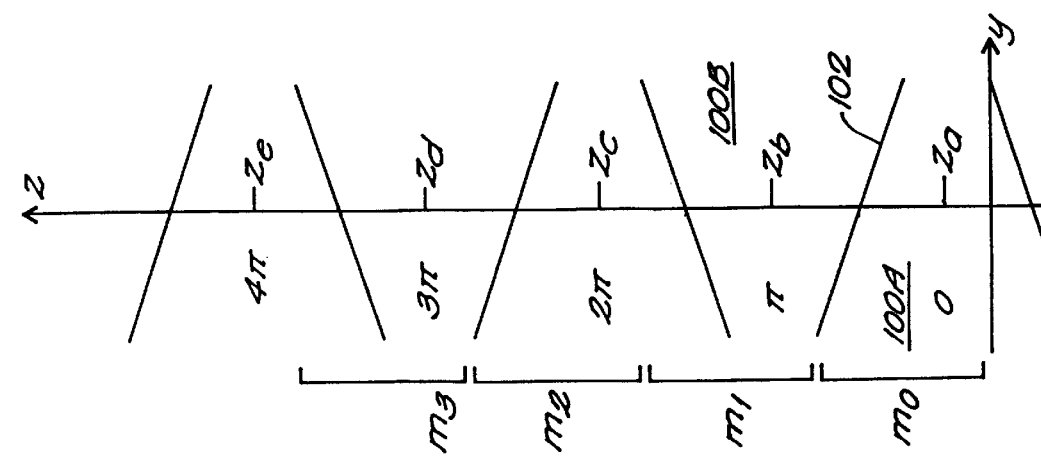

The volumetric image is divided into sections $m_o$, $m_2$, $m_3$, etc. ..., each section including the same number of object slices, m, but located at different z-positions. FIG. 13A is the superimposed projection paths at multiples of the first view angle 0, $\pi$, $2\pi$, $3\pi$; while FIG. 13C represents the last view angle for reconstructing the sections $\pi-\Delta\phi$, $2\pi-\Delta\phi$, $3\pi-\Delta\phi$, ..., where $\Delta\phi$ is the view-angle interval. The division of the sections has the same repetition as the axial fans. As the result, each section can be backprojected in the same manner. A three-dimensional matrix is used to backproject for one section. When the three-dimensional matrix is reconstructed from superimposed projections of view angles ranging from 0 to $\pi-\Delta\phi$, then the same three-dimensional matrix will be used for reconstructing the next section.

The backprojection for section $m_1$, for example, requires two axial fans centered at $Z_c$ and $z_b$ for each column in the initial view angles. At view angle $\phi$, it further requires data for the axial fan centered at $z_a$. Thus, two to three axial fans per column are required for back projecting each section $m_o$ ... $m_3$ at a view angle. It is possible to reduce the requirement to no more than two axial fans by reducing the number of slices per section without changing the slice width. However, because some computations can be shared among these slices, the overall efficiency of the backprojection will be improved with more slices in a smaller number of sections.

B. Overlapping of Axial Fans-Separation Line

The boundary 102 between two superimposed axial fans for example fans 100A and 100B may be slightly overlapped. The extent of overlapping depends on the manner in which the reordered projections $R_{ij}(\phi)$ are interpolated into the constant-z projections $S_{ij}(\phi)$, and also depends on the pitch D used for the helical scan. If the midpoint $c_{ij}$ described above is used to measure the z-position of the projection and the translation distance is $D = m*\Delta h$ as given in Equation 24 over a half rotation of the gantry, the two superimposed axial fans of $S_{ij}(\phi)$ will be perfectly matched without overlapping in every detector column. This is a significant advantage of using the midpoint $c_{ij}$ as the reference point for the constant z-position interpolation.

Figure 15:
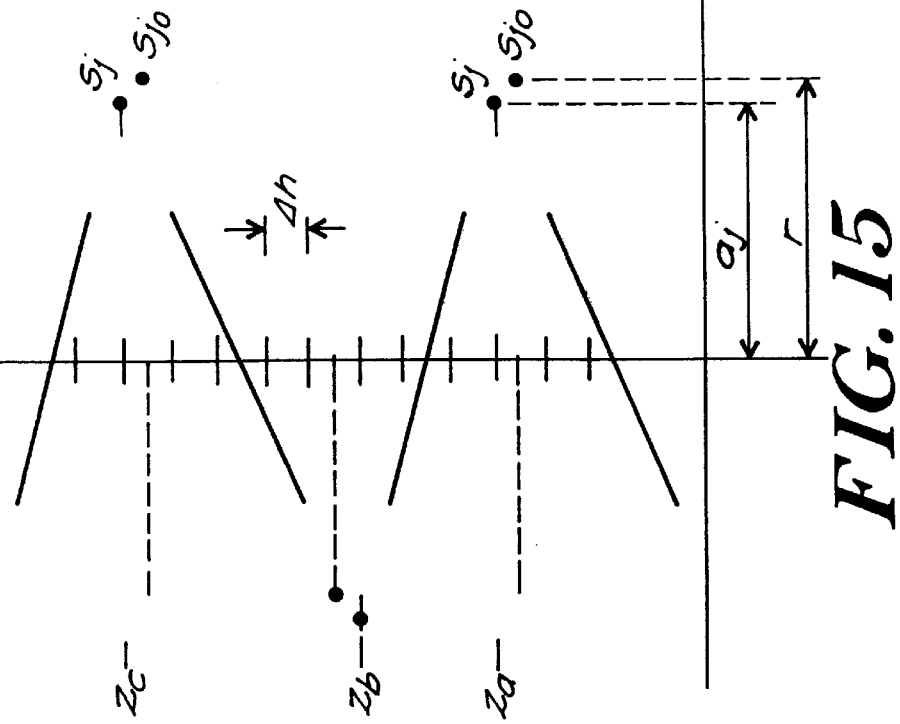
FIG. 15 illustrates the distribution of constant-z interpolated projections $S_{ij}(\phi)$ for a detector column located a distance from the central column, using $c_{ij}$ as the midpoint for purposes of the interpolation, in accordance with the present invention.
Figure 14:
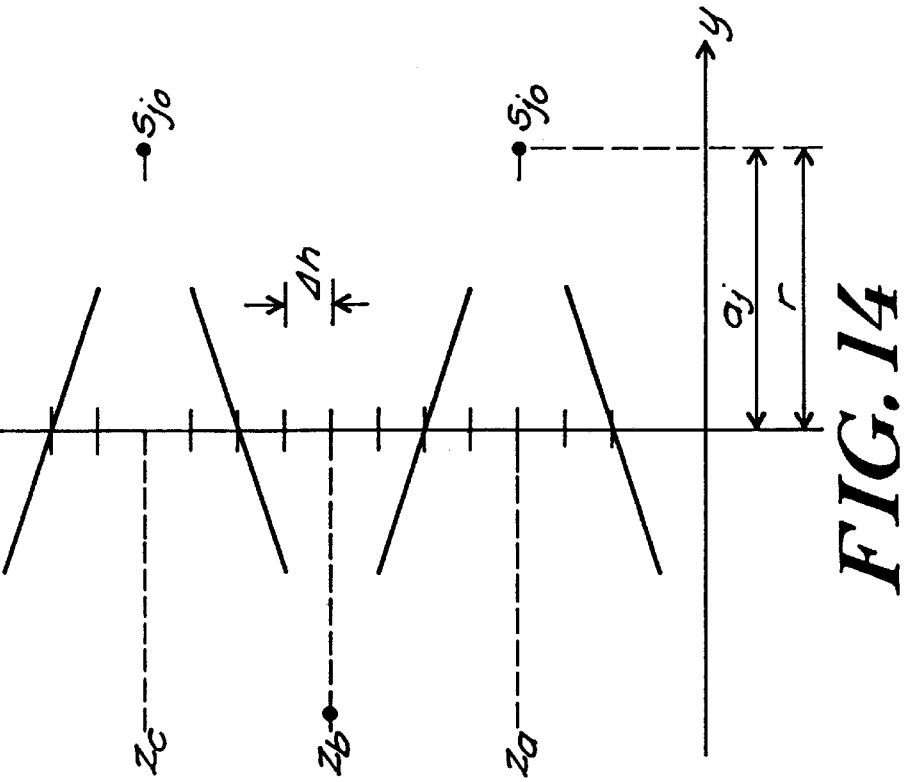
FIG. 14 illustrates the distribution of constant-z interpolated projections $S_{ij}(\phi)$ for the central detector column in accordance with the present invention.

The distribution of $S_{ij}(\phi)$, $S_{ij}(\phi+\pi)$, and $S_{ij}(\phi+2\pi)$ for the central detector column and a detector column located at a distance from the center are shown in FIGS. 14 and 15 respectively in yz-space. The locations of constant-z interval $\Delta h$ are all on the z-axis for $S_{ij}(\phi)$, $S_{ij}(\phi+\pi)$, $S_{ij}(\phi+2\pi)$.

Figure 16:
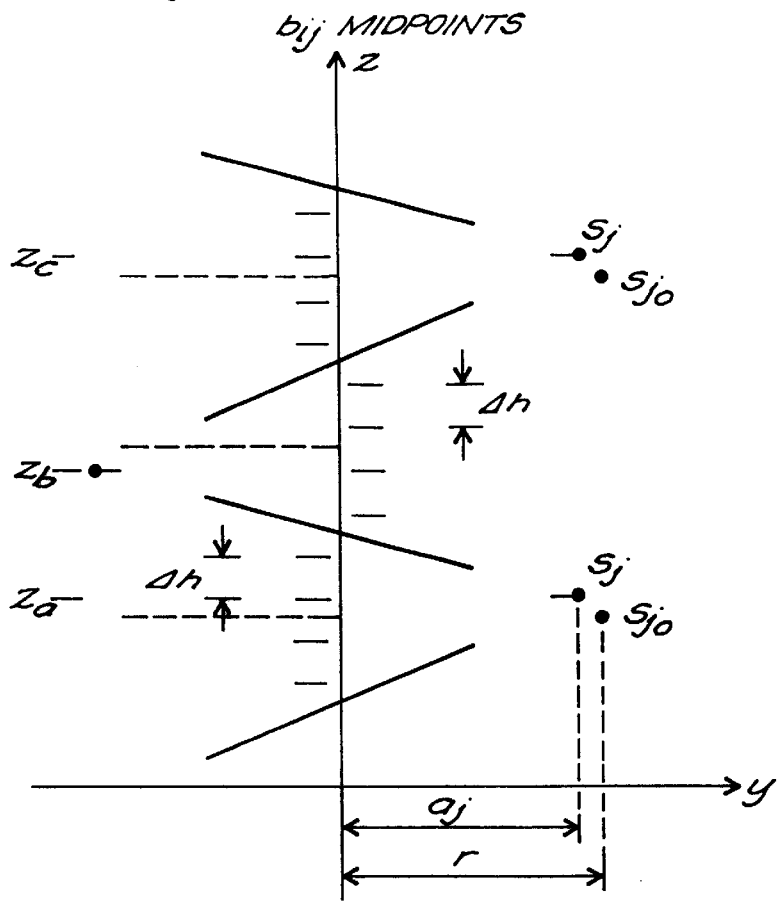
FIG. 16 illustrates the distribution of constant-z interpolated projections $S_{ij}(\phi)$ for a detector column located a distance from the central column, using $b_{ij}$ as the midpoint for purposes of the interpolation, in accordance with the present invention.

If the point $b_{ij}$ of FIG. 9 is used as the reference point for the constant-z interpolation in an alternative embodiment, the distribution of $S_{ij}(\phi)$ for a detector column located far from the central column is illustrated in FIG. 16 for comparison. Unlike that based on the midpoint $c_{ij}$ in FIG. 15, the locations of constant-z intervals $\Delta h$ do not lie on the xz-plane, i.e., y=0, although the distribution for the central column remains the same as in FIG. 14. The inferior distribution of constant-z positions not only requires more computations but also results in less accurate backprojection for the voxels located near the boundary regions.

Figure 17:
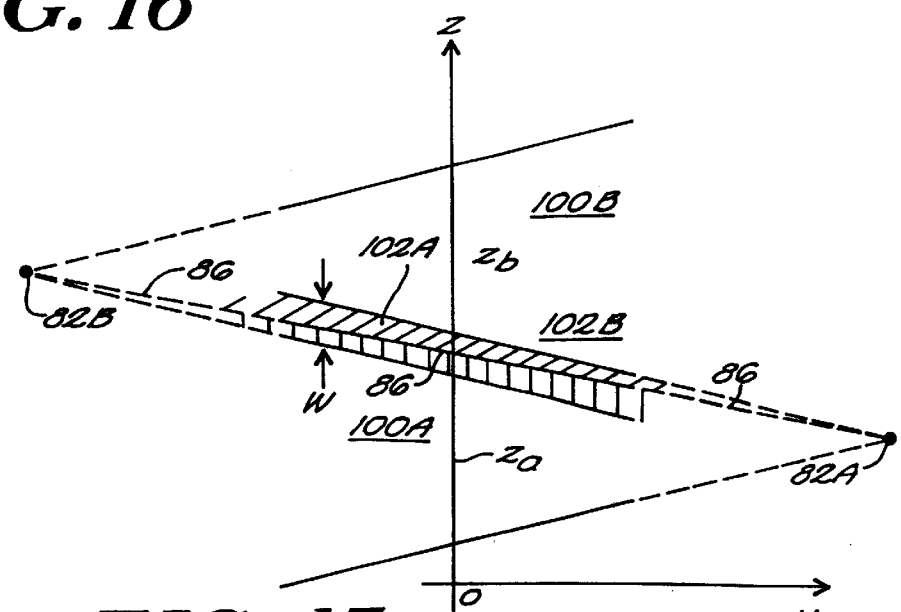
FIG. 17 illustrates the opposing axial fans, where W is the width of the overlapping region and a separation line which limits the extent of each fan for backprojection in accordance with the present invention.

When the pitch is shorter, for example where $D<m*\Delta h$, there will be overlapping in the boundary regions 102. Whether scanning with a pitch of perfect match of the two superimposed axial fans, or a shorter pitch, a separation line 86 is used across the boundary region to separate the axial fans 100A, 100B for backprojection. It is preferable to select the line connecting the two axial-fan sources 82A, 82B as the separation line, as illustrated in FIG. 17 with a slightly overlapped region 102.

The projections of either axial fan 100A, 100B beyond this separation line 86 will not be used for backprojection. For example, the projections corresponding to overlapping region 102A, a portion of axial fan 100A, and projections corresponding to overlapping region 102B, a portion of fan 100B, are removed from consideration. Under this arrangement, the projections within the overlapped region 102A, 102B are uniquely defined. At a view angle $\phi$, a voxel will be located on either side of this separation line 86, and only the projection value from that side of axial fan will be backprojected to the voxel.

The separation lines 86 for different columns are not parallel to each other, because the z-position of the axial fan is column-dependent. Suppose at a given view angle $\phi$ the z-positions of the two opposed axial-fan sources are $z_a$ and $z_b$ as indicated in FIG. 17. The difference between $z_a$ and $z_b$ can be obtained from Equation 16 by letting $i=i_o$ and noting that the columns in filtered projections $U_{ij}(\phi+\pi)$ are in reverse order with respect to $U_{ij}(\phi)$:

$$z_b-z_a=D+2\delta*(j-j_o)*D/\pi \tag{27}$$

The middle position between $z_a$ and $z_b$ can also be obtained from Equation 16 by replacing $\phi$ with $\phi+\pi$ for $z_b$ and setting $i=i_o$, $$(z_b+z_a)/2=D/2+\phi*D/\pi \tag{28}$$

Using Equations 27 and 28, the z-coordinate of the separation line $z_{sj}$ can be calculated as a function of the y-coordinate from $$z_{sj}=(z_b+z_a)/2-y*(z_b-z_a)/2a_j \tag{29}$$

In Equations 29 and 16, the position of the central row of $U_{ij}(\phi)$ is at z=0 when $\phi=0$. That is $z_{sj}=0$ when $\phi=0$. An offset $z_o$ is added to Equation 26 in general cases as $$z_{sj}=z_o+(z_b+z_a)/2-y*(z_b-z_a)/2a_j \tag{30}$$

where $z_o$ is the $z_a$ value at view angle $\phi=0$, and $a_j$ is given by Equation 9.

C. Backprojection in Two Stages

The next step of the inventive process involves backprojection in two stages, each involving an interpolation. The first interpolation stage is based on the x position of the voxels. The corresponding column $j_x$ is calculated and the filtered projection value $Uij_x$ is interpolated from adjacent columns $U_{ij}$ and $U_{i,j+1}$, where $j \leq j_x < j+1$, for each row of the superimposed projections. The second stage is based on the y and z-positions of each voxel. The corresponding row $i_z$ of the projection passing through the location (y,z) is calculated and the projection value $Ui_zj_x$ is interpolated from $Uij_x$ and $U_{i+1}j_x$, with $i \leq i_z < i+1$. The bilinear interpolated projection $Ui_zj_x$ is then preferably used to backproject for the voxel.

Figure 18:
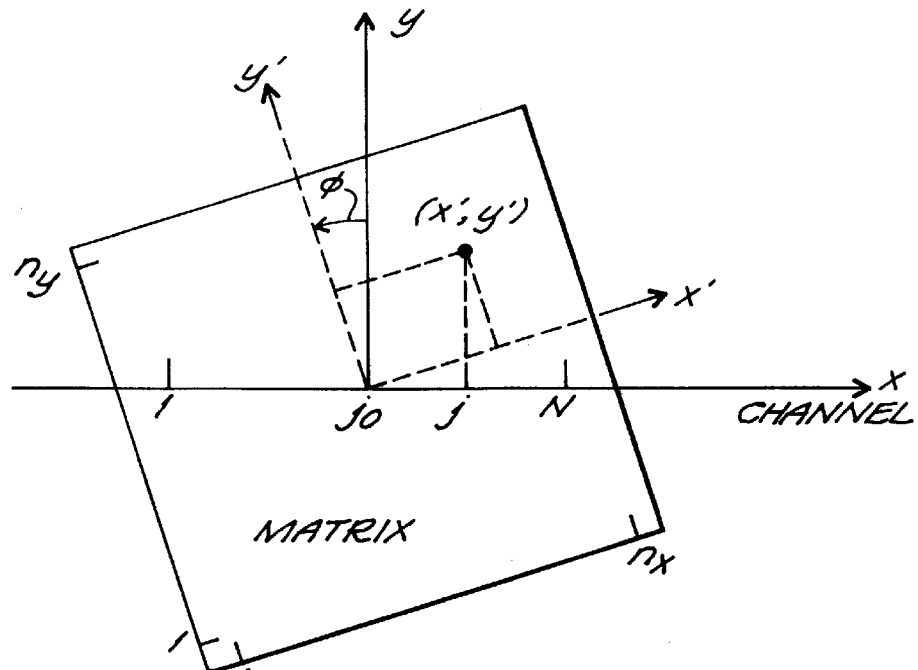
FIG. 18 illustrates reconstruction of a section of the object in a coordinate system (x',y',z') fixed in object space, and illustrates the geometry of the first stage interpolation of backprojection in accordance with the present invention.

To reconstruct a section of the object, a coordinate system x'y'z' fixed in the object space is used as shown in FIG. 18. Assuming there are m slices on the x'y' planes in the three-dimensional matrix of voxels representing the object. For a view angle $\phi$, this coordinate system is rotated about the z'-axis with respect to the coordinate system xyz for the angle $\phi$, with the z'-axis coincides with the z-axis. The location of a voxel with respect to the gantry, that is the coordinate (x,y), can be calculated from the location of the voxel in the object coordinate (x',y'). The z-positions are not changed by the rotation, and those voxels with the same (x',y') locations from different slices will have the same (x,y) coordinate.

D First Stage Interpolation The first-stage interpolation in the x-dimension for $Uij_x$ is commonly used in the conventional two-dimensional parallel-beam reconstruction. If (x', y',z') is the coordinate of a voxel at rotation angle of $\phi$, then $$x=x'\cos(\phi)+y'\sin(\phi)$$

$$y=y'\cos(\phi)-x-\sin(\phi)$$

$$z=z' \tag{31}$$

FIG. 18 illustrates the coordinate (x,y) of a voxel located at (x',y'). The coordinate x is converted to a corresponding column number $$j_x=j_o+x \tag{32}$$

where $j_o$ is the central column number. The interpolated projection can be calculated by linear interpolation as $$Uij_x=(j+1-j_x)*U_{ij}+(j_x+j)*U_{ij+1}$$

where $$j \leq j_x < j+1 . \tag{33}$$

Figure 19:
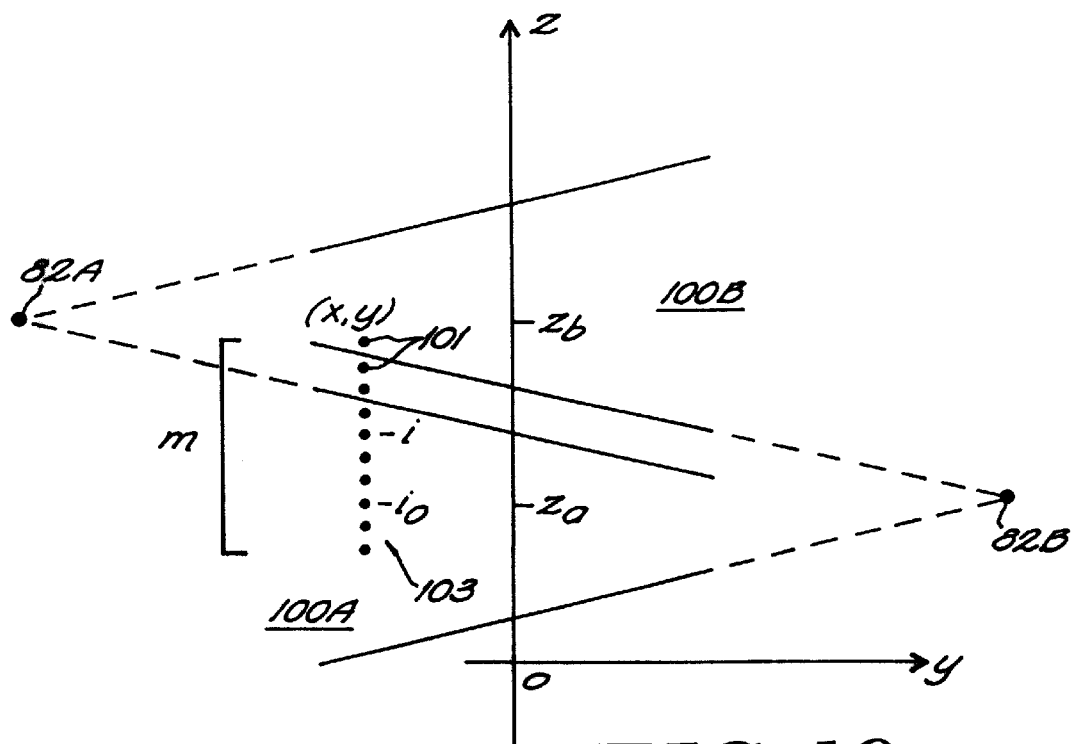
FIGS. 19, 20A and 20B illustrate the geometry of second stage interpolation of backprojection in accordance with the present invention.

The interpolation is performed for both superimposed axial fans. In other words, Equation 33 is used to interpolate for $Uij_x(\phi)$ 100A and $Uij_x(\phi+\pi)$ 100B which lies within the z dimension of the matrix. For example, a column of voxels 103 with the same (x,y) coordinates but different z-coordinates are marked in dots in FIG. 19. In this example, most of these voxels will be backprojected from $U_{ij}(\phi)$ 100A, but the two voxels 101 at the highest z-coordinate will be backprojected from $U_{ij}(\phi+\pi)$ 100B.

E. Second Stage Interpolation

Figure 20A:
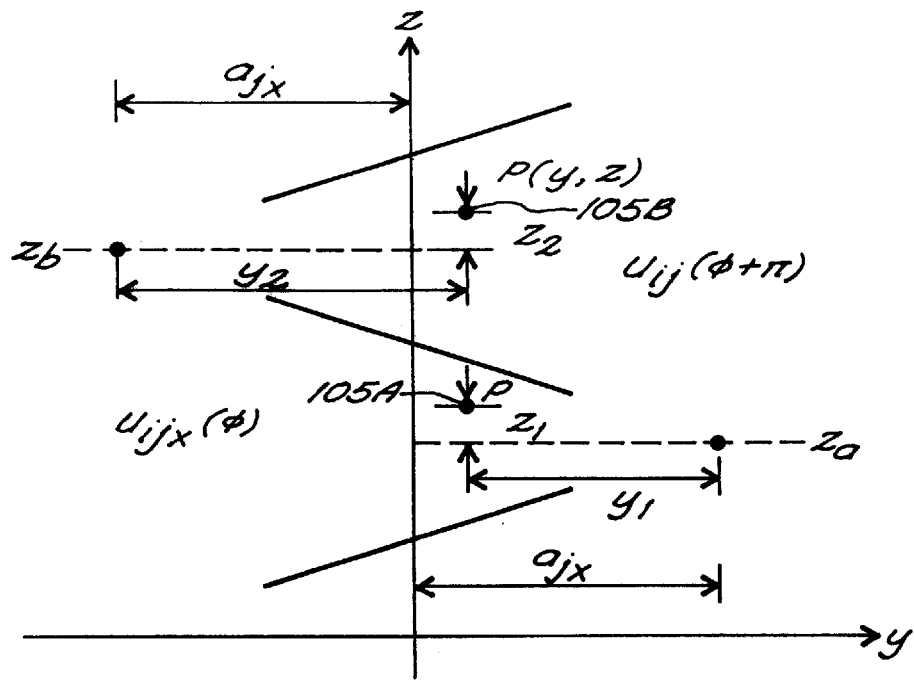

The second-stage interpolation for $Ui_zj_x$ in yz space is more sophisticated than the first stage. Given the coordinate (y,z) of a voxel, the corresponding row number $i_z$ of the projection $Ui_zj_x$ which passes through the voxel must first be determined. This row number $i_z$ can be calculated from the z position of the projection $Ui_zj_x$, that is the z-axis intercept of $Ui_zj_x$. Let $y_1$ and $z_1$ represent the distance of the voxel 105A measured from the X-ray source of $Uij_x(\phi)$ diverging from a focal point at a positive y-axis position of $y_a=a_{jx}$, as shown in FIG. 20A. Similarly, let $y_2$ and $z_2$ represent the distance from the voxel 105B measured from the X-ray source of $Uij_x(\phi+\pi)$ diverging from a focal point at a negative y-axis position of $y_b=-a_{jx}$. From this figure it is clear that $$y_1=a_{jx}-y$$

$$z_1=z-z_a \tag{34}$$

for $Uij_x(\phi)$ and $$y_2=a_{jx}+y$$

$$z_2=z-z_b \tag{35}$$

for $Uij_x(\phi+\pi)$.

Figure 20B:
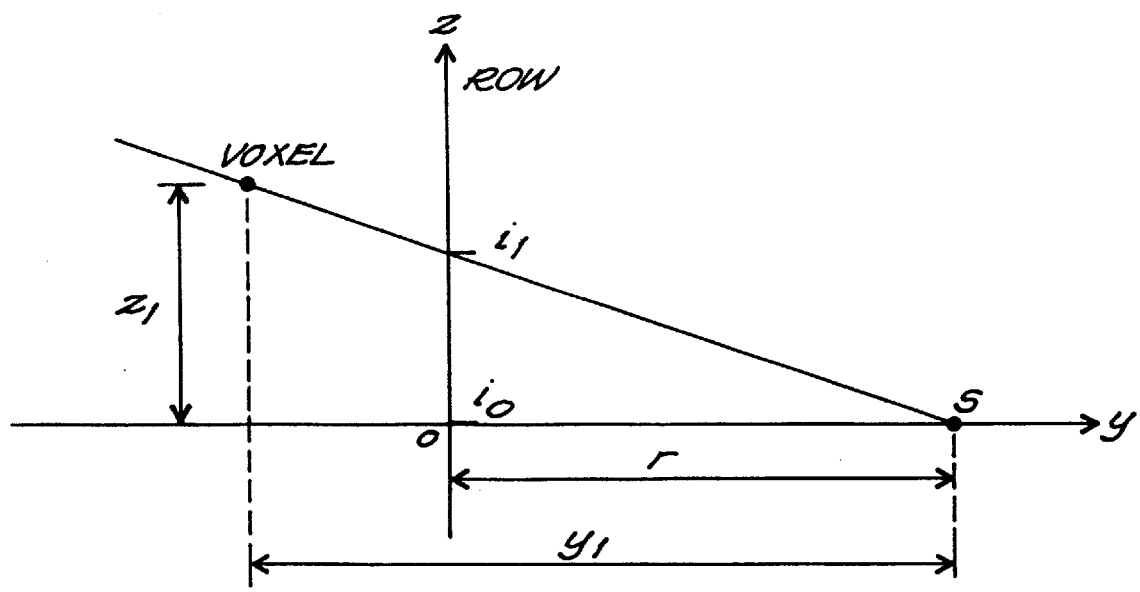

The X-ray paths are separated by equal spatial intervals when they are measured along the z direction. FIG. 20B illustrates the $Uij_x(\phi)$ projection path passing through the voxel at $(y_1,z_1)$. The intercept of the path on the z-axis is $$i_1 i_{o1}=z_1*a_{jx}/y_1 \tag{36}$$

where $i_{o1}$ is the central row number of $Uij_x(\phi)$ Equation 36 provides the increment of row number with respect to increment in z-coordinate of the voxel, $$\Delta i_1 = \Delta z_1 * a_{jx}/y_1 \tag{37}$$

If the z-dimension of the matrix is chosen to be the same spacing as the intercept of X-ray paths on the z-axis, then $\Delta z_1=1$. The row increments for $Uij_x(\phi)$ and $Uij_x(\phi+\pi)$, respectively become $$\Delta i_1 = a_{jx}/y_1$$

$$\Delta i_2 = a_{jx}/y_2 \tag{38}$$

For fast computation, $\Delta i_1$ and $\Delta i_2$ can be obtained from a lookup table based on $y_1$ and $y_2$.

The location of $z_{sjx}$ of the separation line between these two axial fans can be calculated from Equations 27, 28, and 30, by using $j=j_x$ and y from Equation 31.

For voxels with z locations of $0 \leq z < z_{sjx}$, the axial fan $Uij(\phi)$ is interpolated for backprojection. The interpolating row number is computed from $$i_z = i_{o1} + z_1 * \Delta i_1 \tag{39}$$

with $z_1$ and $\Delta i_1$ given by Equations 34 and 38.
The final projection value for backprojection is then $$Ui_zj_x(\phi)=(i+1-i_z)*Uij_x(\phi)+(i_z-i)*Ui,j_{x+1}(\phi)$$

where $$i \leq i_z < i+1 \tag{40}$$

For voxels with z locations of $z_{sjx} \leq z < m$, the other axial fan $Uij_x(\phi+\pi)$ will be interpolated for back-projection. The interpolating row number is computed from $$i_z = i_{o2} + z_2 * \Delta i_2 \tag{41}$$

where $i_{o2}$ is the central row number of $Uij_x(\phi+\pi)$. The final projection value for backprojection is $$Ui_zj_x(\phi)=(i+1-i_z)*Uij_x(\phi+\pi)+(i_z-i)*Ui,j_{x+1}(\phi+\pi)$$

with $$i \leq i_z < i+1 \tag{42}$$

VII. Improved Detector Array Geometry

The above descriptions and illustrations are based on a symmetric cylindrical detector array, referred to hereinafter as a detector array of standard geometry. Detector arrays in other geometries are possible and may be preferable with appropriate modifications.

As an example, for the detector array of standard geometry shown in FIG. 2, the aforementioned technique of constant-z interpolation limits full usage of the acquired data, because a portion of the projection data derived from the near top rows 56A and bottom rows 56C of detector elements 53 are out-of-bounds for this interpolation. This can be seen more clearly from FIG. 11. The projections marked in circles 92 are reordered projections $R_{ij}$ collected from the detectors in the first row of detector elements 53. As a result of the translation in the helical scan, the reordered projections $R_{ij}$ do not lie in a plane perpendicular to the z-axis. In contrast, the projections marked in squares are the first row of constant-z-interpolated projections $S_{ij}$, which do substantially lie in a plane perpendicular to the z-axis to maintain the required constant-z position. If any z position beyond $S_{ij}$ is selected for constant-z interpolation of, for example, $S_{oj}$, a portion of $S_{oj}$ would be out of the region of reordered projections and could not be properly interpolated. Unlike the interpolated projections between the first row and last row of $S_{ij}$, the partially interpolated projections $S_{oj}$ do not include all projections passing through the entire transaxial section of the object. They cannot be used to reconstruct the image as required by the filtered backprojection method.

Consequently, the reordered projections $R_{ij}$ lying in the triangular region 91A of FIG. 11 between $R_{ij}$ and $S_{ij}$ are extra data which cannot be used for the constant-z interpolation and subsequent operations. These extra data come from detectors in upper left corner of detector elements 53, and they are considered out-of-bounds for reconstructing the image of the object. Likewise, the reordered projections $R_{ij}$ in the lower triangular region 91B of FIG. 11 are out-of-bounds data that are derived from the detectors in the lower right corner of the array. As a result of the out-of-bounds data, the maximum pitch of the helical scan is less than that which would otherwise be expected from the physical dimension of the detector array. Instead of translating the object over the distance defined by all rows of the detector array in a half rotation of the gantry, the object can only be translated for about two-thirds of that distance.

The deficiency in the usage of the acquired data and the reduction in the pitch can be rectified by configuring the detector array in a more favorable geometry in accordance with the present invention. Several alternative techniques for accomplishing this are described below.

Figure 21A:
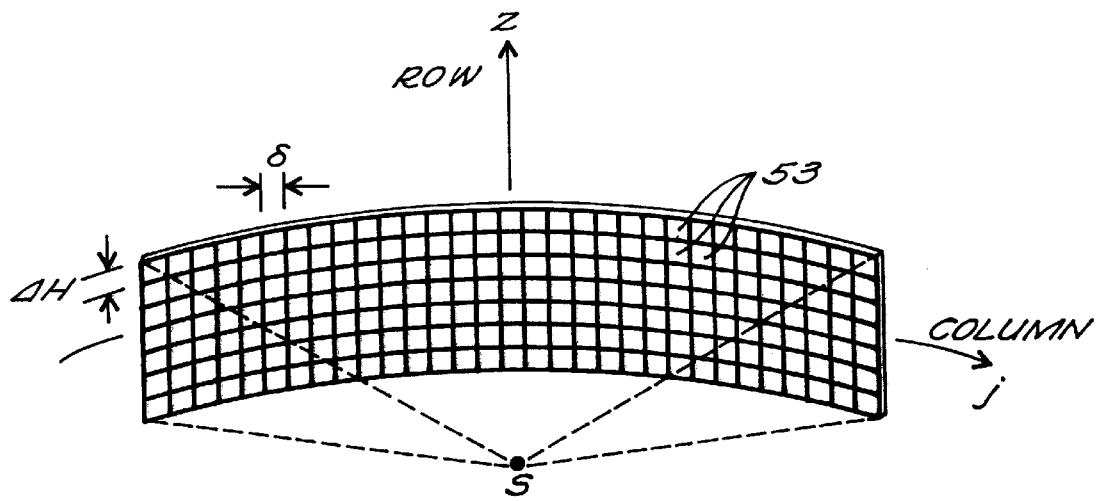
FIG. 21A is a perspective view of an example of a symmetric cylindrical detector array, including 7 rows and 31 columns of detector elements, suitable for tomographic imaging of objects in accordance with the inventive techniques described above.
Figure 21B:
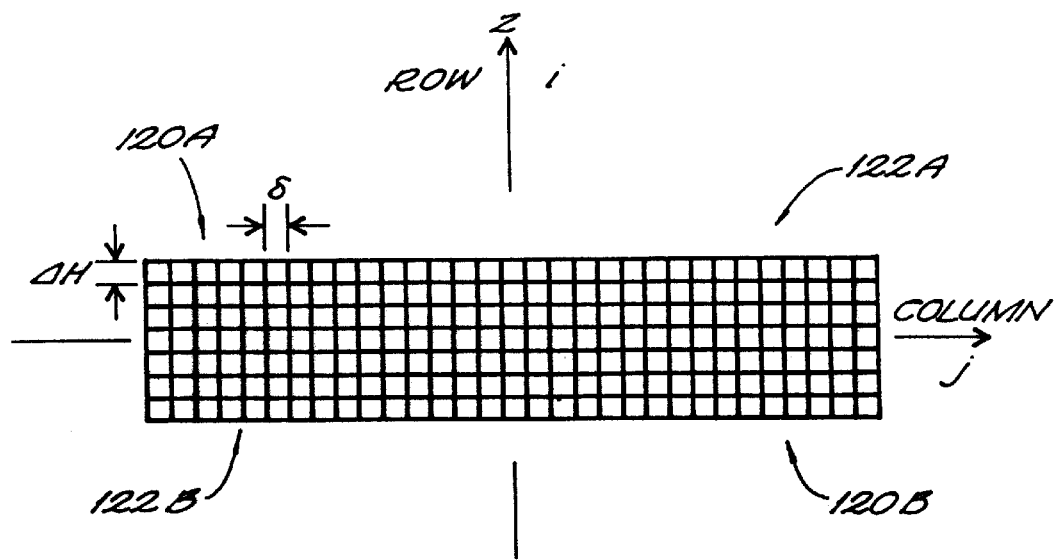
FIG. 21B is the cylindrical detector array of FIG. 21A, drawn in two-dimensional form.

A standard symmetric cylindrical detector array having, for example, 7 rows and 31 columns, as shown in FIG. 21A, is used as an example for the following discussion. In practice, the number of columns j is usually much greater than the number of rows i, and the number can be even or odd. A two-dimensional illustration of the same detector array is given in FIG. 21B to illustrate the relative locations and rectangular spatial relationship of the detectors 53.

For illustrative purposes in connection with the remaining FIGS, the direction of relative translation of the object is assumed to be in the direction of the arrow defining the translation direction of the positive z-axis, while the leading edge of the detector array (the direction of rotation) is considered the leftmost edge of the detectors.

The out-of-bounds data due to constant-z interpolation are obtained from those detector elements near the two opposite corners 120A, 120B (the rear leading and front trailing corners of the detector array) for every rotation angle. In accordance with one aspect of the invention, the detector elements in these out-of-bounds areas 120A, 120B can be depopulated, or the two opposite corners 122A, 122B (the front leading and rear trailing corners of the detector array) can be overpopulated, or both, to make full use of the data collected by every detector element in the array.

Figure 22A:
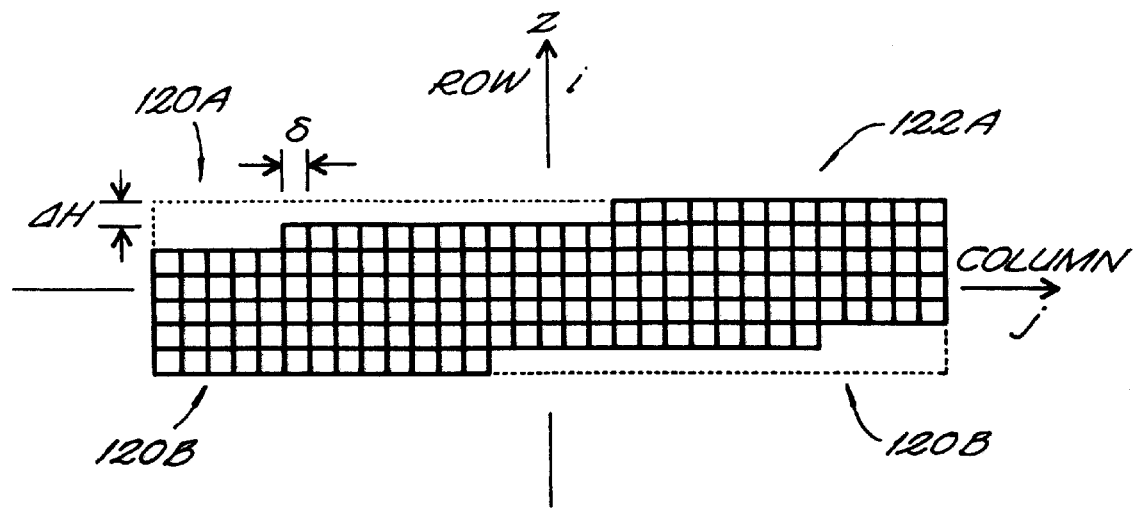
FIG. 22A illustrates the detector array of FIGS. 21A and 21B, wherein unneeded detector elements, for example detectors which do not contribute to image quality, are depopulated in accordance with the present invention.

A detector array having a depopulated configuration is illustrated in FIG. 22A. This array has the same number of detector columns j as the standard geometry illustrated in FIG. 21A; however, the top and bottom rows i are only partially populated. All the mathematical equations of the standard geometry defined above in connection with the constant-z interpolation technique are applicable to the depopulated configuration of FIG. 22A. The only difference is that the out-of-bounds data (not used for backprojection in any event) in regions 120A, 120B are invalid.

Figure 22B:
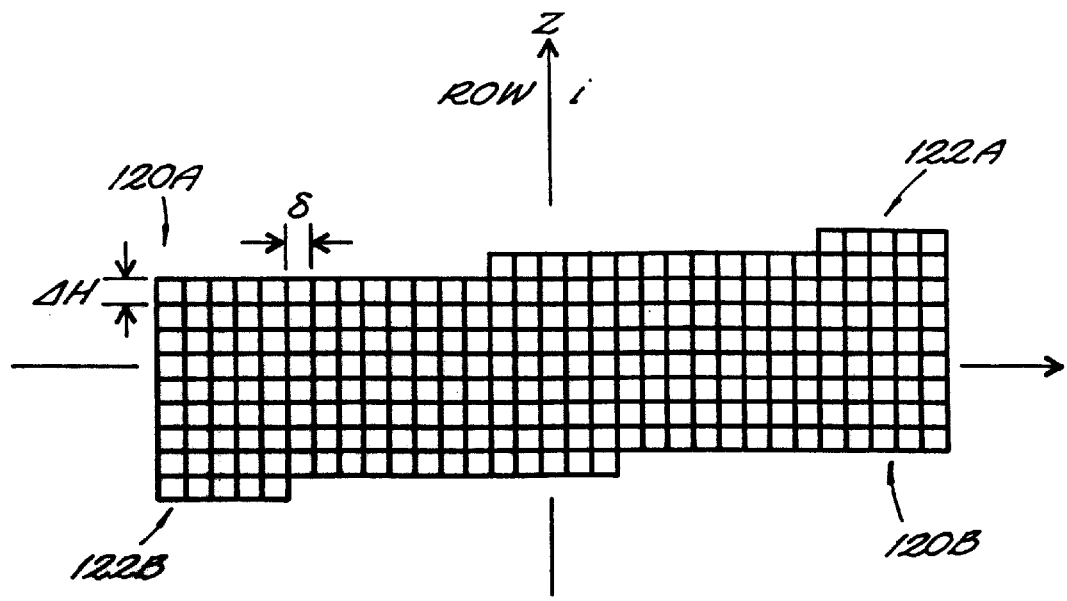
FIG. 22B illustrates a detector array wherein additional detector elements are populated in active regions of the array in accordance with the present invention.

A detector array having an overpopulated configuration is shown in FIG. 22B. In this configuration, detector elements are added to opposite corners 122A, 122B of the array, and the data from all detectors are valid for backprojection. The effective number of rows i of the detector array is increased without populating all elements of the outer rows.

Figure 23:
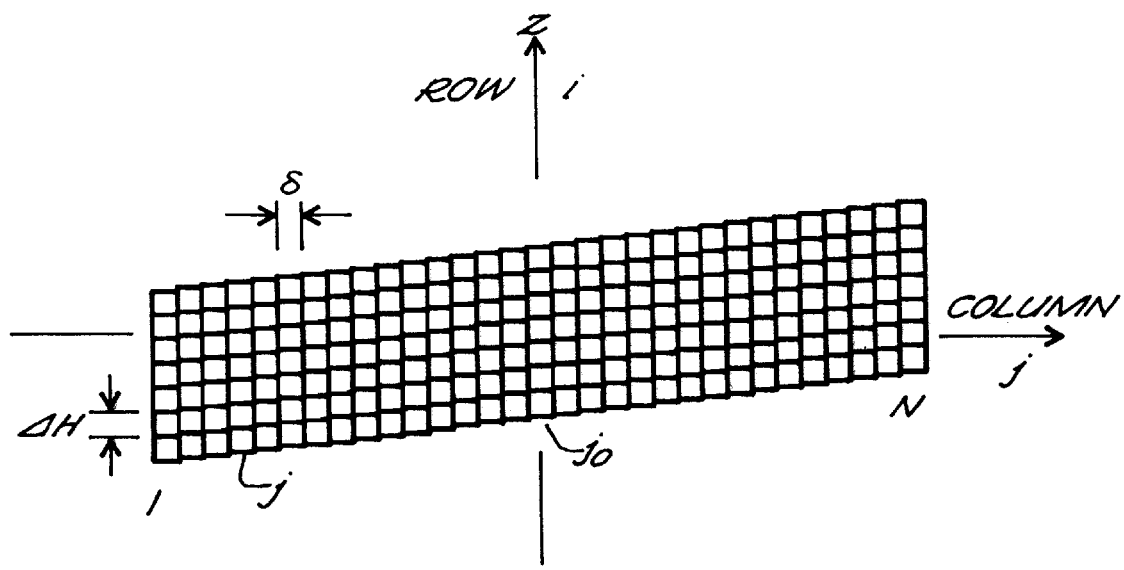
FIG. 23 is an illustration of a detector array having a relative shift in z-position along the transition axis for each column in accordance with the present invention.

In a second preferred configuration, illustrated in FIG. 23, detectors in the same row have different z-positions; in other words the detector array is configured to be column-dependent with respect to z position along the translation axis. Each column j is shifted along the z-direction by an amount such that the detectors of the same row i correspond with a helical path along the cylindrical surface. More precisely, the detector at row i and column j is placed at the z location $H_{ij}$ of $$H_{ij}=(i-i_o)*\Delta H+(j-j_o)*\delta*D*R/(\pi*a_j). \tag{43}$$

Where the variables are defined as before. In particular, $\Delta H$ is the spatial interval between adjacent rows of detectors and $\delta$ is the angular interval between adjacent column of detectors. From Equations (10) through (13), the z-coordinate of the midpoint $c_{ij}$ in this shifted configuration becomes:

$$z_{ij}=(i-i_o)*\Delta h*a_j/r+(j-j_o)*\delta*D/\pi. \tag{44}$$

From Equation (14), the z-position of the fan-beam projection $P_{ij}(\theta)$ for this shifted configuration becomes:

$$z_{ij}(\theta)=(i-i_o)*\Delta h*a_j/r+(\theta)+(j-j_o)*\delta*D/\pi. \tag{45}$$

as compared to Equation (15) for the standard configuration. The z-position of the reordered parallel beam projection $R_{ij}(\phi)$ for the shifted configuration then becomes:

$$z_{ij}(\phi)=(i-i_o)*\Delta h*a_j/r+\phi*D/\pi. \tag{46}$$

as compared to Equation 16 for the standard geometry.

Figure 24:
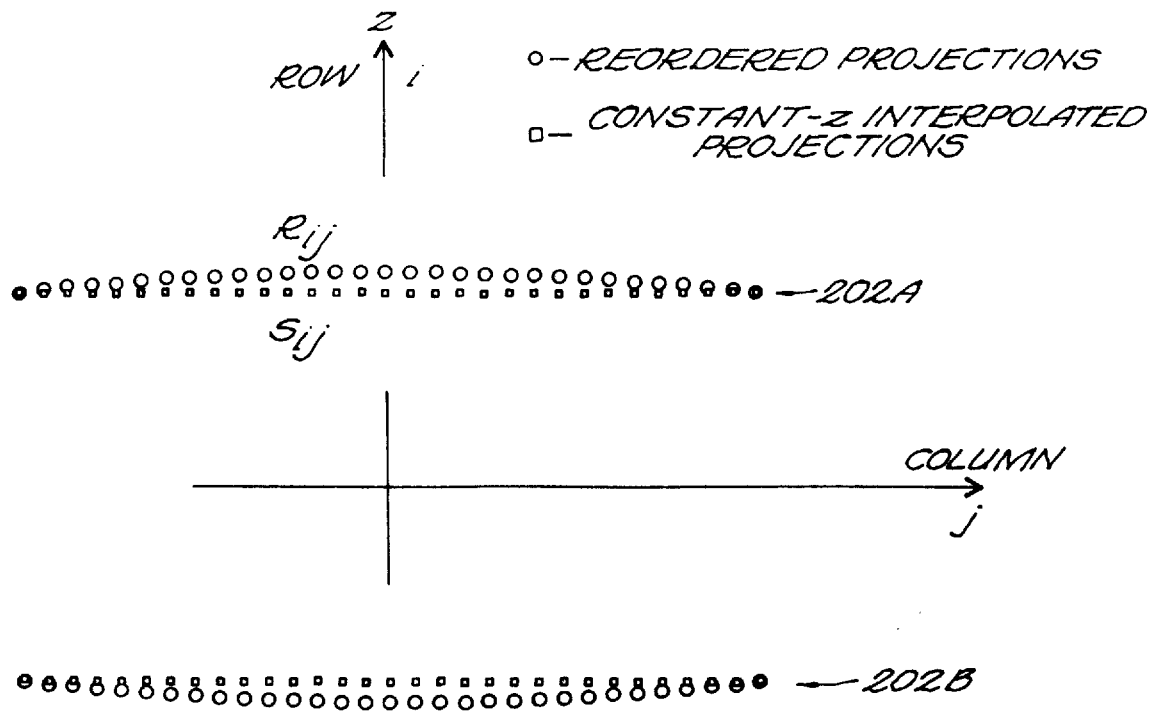
FIG. 24 depicts the relative z-position of the first and last rows of projection data from the detector array of FIG. 23 prior to and following constant-z interpolation.

The factor $a_j/r$ corresponds to 1.0 near the central column $j=j_o$. If the fan angle of the transaxial fan, i.e., $2\gamma_{max}$, is 60°, the worst case of factor $a_j/r$ is cos 30°=0.866 for j=1 or j=N. Therefore, as indicated in Equation 46, the reordered projections $R_{ij}(\phi)$ have a near constant z-position for each row of projections near the central region. The above-described technique of constant-z interpolation is still preferred for this embodiment, but it does not have as much of an advantageous effect on those columns near the central column $j_o$. For the columns j most distant from the central column $j_o$, the constant-z interpolation is as important as in the standard geometry of FIG. 21A. However, in the worst case, the z location of the interpolating point differs from the collected data point by only about 15% of the distance $(i-i_o)\Delta h$. This means that a relatively small number of detectors are out of bounds in this configuration. The z locations of the top and bottom rows of the reordered projections $R_{ij}(\phi)$ and the constant-z interpolated projections $S_{ij}(\phi)$ are depicted in FIG. 24 for comparison with the standard geometry in FIG. 11. Because only the top and bottom rows 202A, 202B are shown, it may appear that the constant-z interpolated projections $S_{ij}$ deviate most from the reordered projections $R_{ij}$ to the largest extent near the center column $j_o$. In fact, near the central column, an interpolated projection $S_{ij}$ derived from row i can have close proximity to $R_{ij}$ of an adjacent row i'. The proximity depends on the interpolation interval chosen.

If each column is shifted by an amount $(j-j_o)*\delta*D*R/(\pi*r)$ such that:

$$H_{ij}=(i-i_o)*\Delta H+(j-j_o)*\delta*D*R/(\pi*r), \tag{47}$$

then instead of Equation 43, the z-coordinate of the point $b_{ij}$ is represented by:

$$h_{ij}=H_{ij}*r/R=(i-i_o)*\Delta h+(j-j_o)*\delta*D/\pi. \tag{48}$$

Therefore, with reference to FIGS. 8 and 9, and corresponding discussion, if $b_{ij}$ is used as the midpoint for the constant-z interpolation instead of $c_{ij}$, the z-coordinate of the midpoint $b_{ij}$ is $z_{ij}=h_{ij}$, and the z position of the reordered projections $R_{ij}(\phi)$ becomes:

$$z_{ij}(\phi)=(i-i_o)*\Delta h+\phi*D/\pi. \tag{49}$$

Under such conditions, the reordered projections $R_{ij}(\phi)$ will have a constant z-position for each row of projections, and constant-z interpolation is no longer needed. However, $b_{ij}$, rather than $c_{ij}$, is preferably used as the midpoint of the projection paths during the backprojection process.

Figure 25:
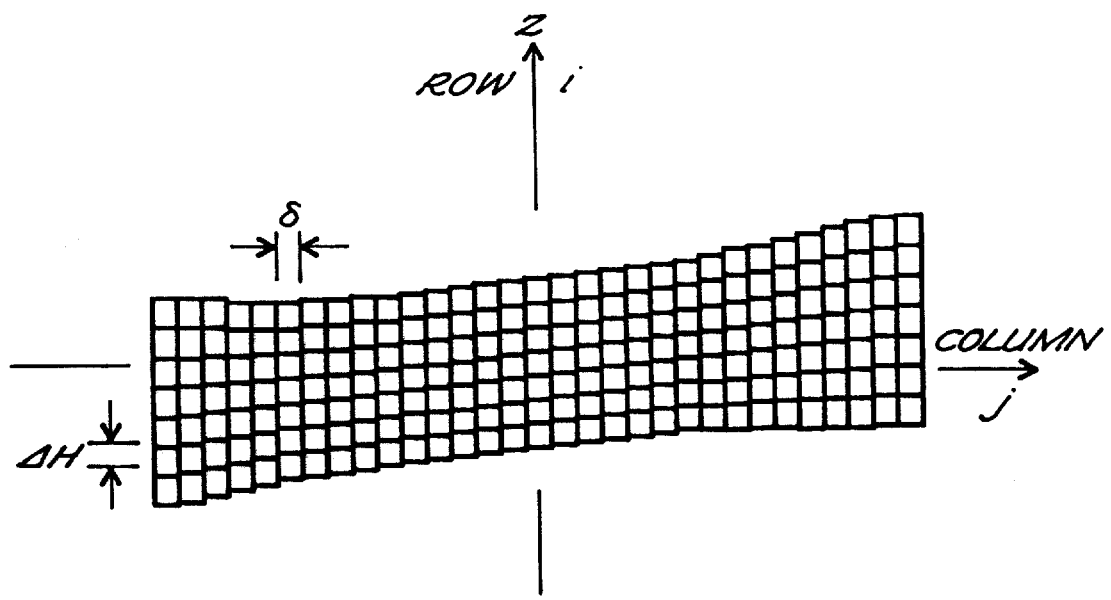
FIG. 25 illustrates a detector array having a relative shift and elongation in z-position along the translation axis for each column in accordance with the present invention.

As illustrated in FIG. 25 in an alternative embodiment, each column is not only shifted with respect to the translation axis as in the FIG. 23 embodiment, but the elements of a column are also elongated, or stretched along the z dimension such that the z location of a detector at row i and column j is placed at $$H_{ij}=(i-i_o)*\Delta H*r/a_j+(j-j_o)*\delta*D*R/(\pi*a_j). \tag{50}$$

The geometry of this configuration eliminates the factor $a_j/r$ in Equation 45, and the z-position of the reordered projection $R_{ij}(\phi)$ becomes:

$$z_{ij}(\phi)=(i-i_o)*\Delta h+\phi*D/\pi. \tag{51}$$

This is an ideal configuration, in which the reordered projections $R_{ij}(\phi)$ have a constant z-position for every row of projections. All acquired data are fully utilized, and there is no need for constant-z interpolation. The factor $r/a_j$ in the first term of Equation 50 is the stretch factor. It is equal to 1.0 for the central column $j=j_o$ and gradually increases toward both ends of the array. For columns at the extreme ends of the array, j=1 or j=N, the dimension of the column is elongated to the maximum factor of 1.0/cos 30°=1.155 (assume transaxial fan angle of 60°) while maintaining the same number of detectors as the central column.

Figure 26:
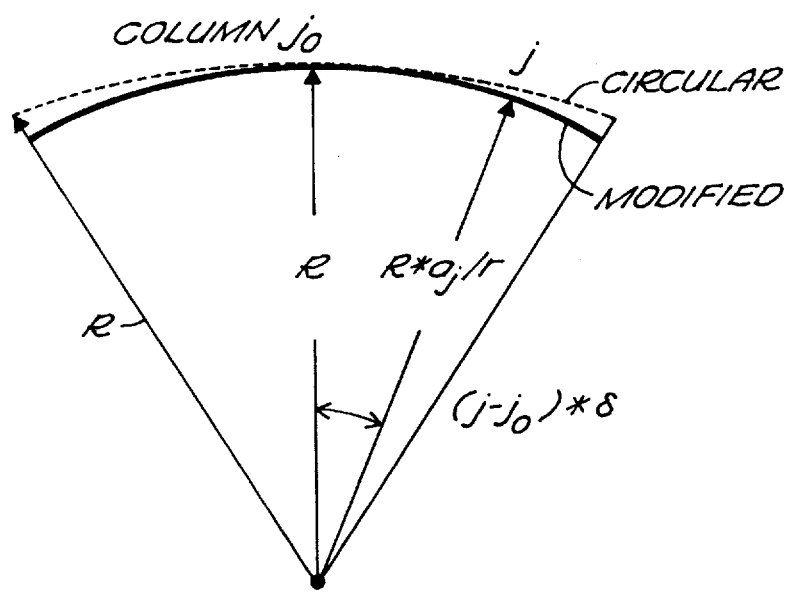
FIG. 26 is a top view of a detector array having column-dependent distance to the X-ray source in accordance with the present invention.

In an alternative configuration illustrated in the top view of FIG. 26, each column is shifted along the z-direction according to Equation 43, and those columns further away from the center column $j_o$, are placed closer to the X-ray source S. For example, the detector rows may follow a modified contour which deviates slightly from a circular contour. The preferred distance between column j and the X-ray source in this embodiment is $R_j=R*a_j/r$. At this distance, the axial fan angle of a column, as seen by the X-ray source, is enlarged to the same degree as that given by the stretch factor described above. Therefore, without physically stretching each column of detectors, this configuration achieves the same ideal condition, in which the reordered projections have a constant z-position for every row of projections.

It should be noted that each of above configurations modified from the standard geometry are optimized for one particular pitch of 2D. Whether by altering the spatial distribution or location of the detectors, the extent of modification depends on the magnitude of D in achieving the least number of out-of-bounds data or minimum degree of constant-z interpolation.

Figure 27A:
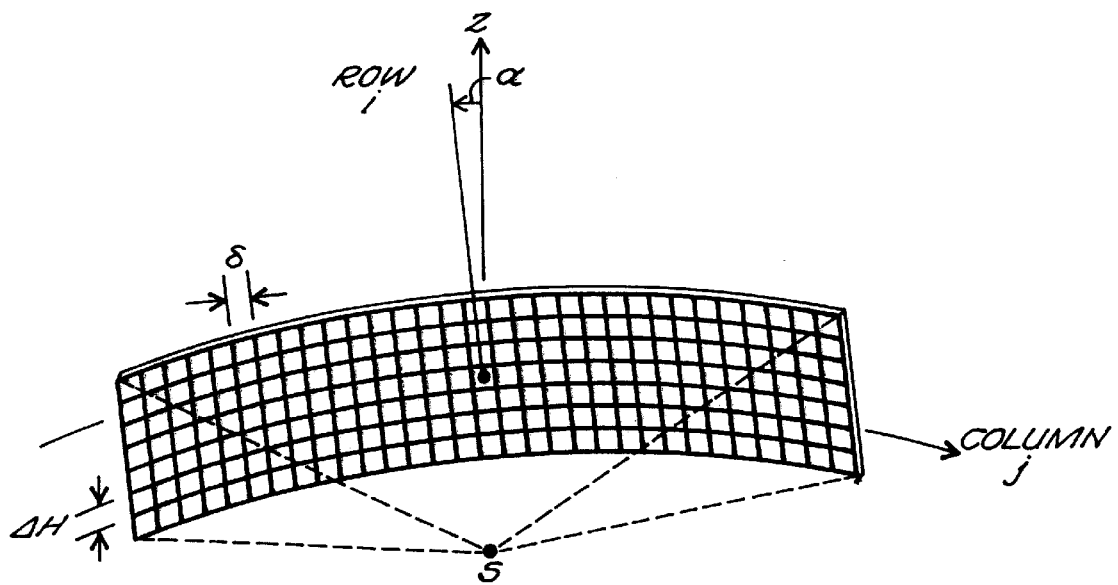
FIG. 27A is a perspective view of a standard symmetric detector array as in FIG. 21A rotated at a small tilt angle a about the y axis in accordance with the present invention.
Figure 27B:
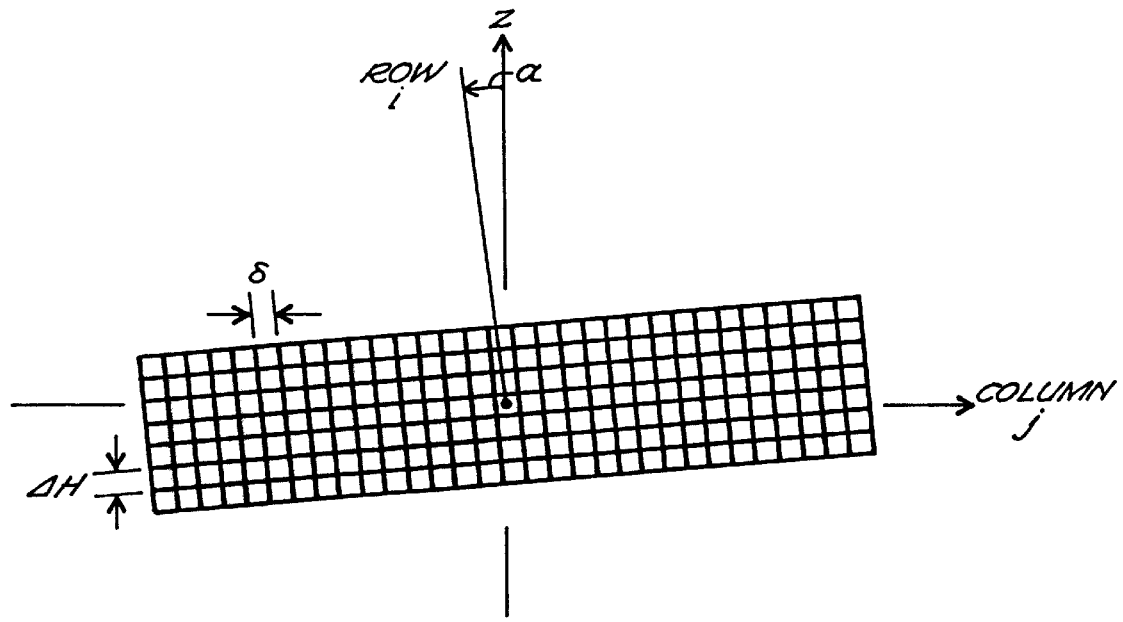
FIG. 27B is the tilted detector array of FIG. 27A drawn in two-dimensional form in accordance with the present invention.

In an alternative embodiment illustrated in FIG. 27A, the detector array is configured in a standard geometry; however it is installed in the gantry at a small angle $\alpha$, where $\alpha \neq 0$, referred to as a tilt angle, rotated about the y-axis or beam-axis (from a position where each row of detectors is disposed within or lies parallel to the x-y plane), where the beam-axis is the axis defined by the X-ray source and the center of the detector array. The detector array and angle a are preferably variably positioned on a rotatable mount 207 driven by motor 203 and controller 205. Because of the tilt angle $\alpha$, the z-position and the angular position of each detector is both row and column dependent. A preferred tilt angle $\alpha$ is small, for example less than 5°. It is a fair approximation to consider the cylindrical detector array as a planar detector array with equal angular spacing $\delta$ between columns, as shown in FIG. 27B, for computing the z-position and angular position of the detectors.

Figure 28:
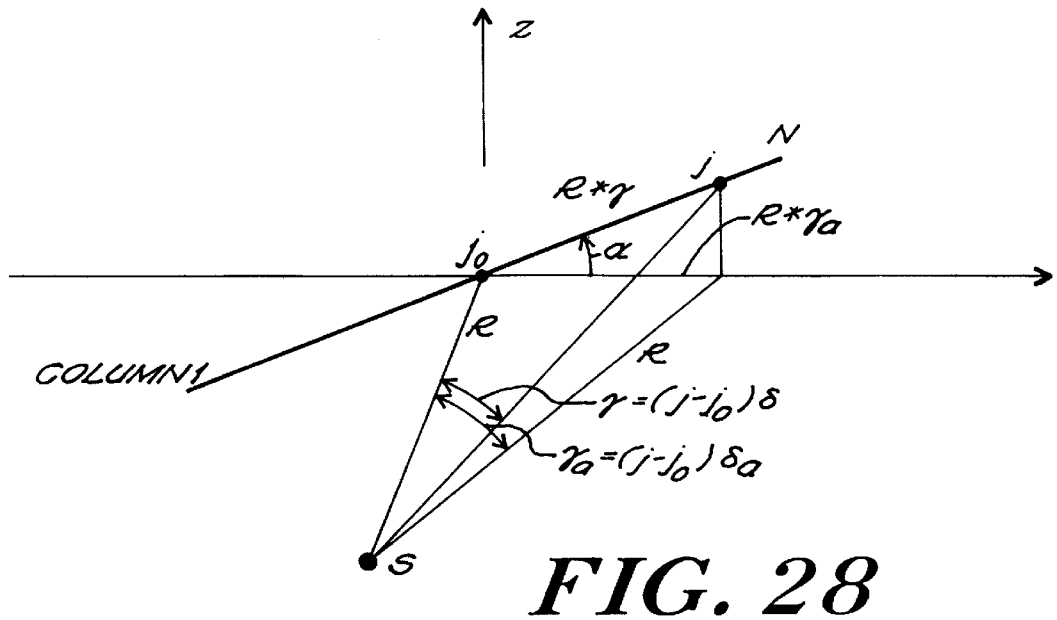
FIG. 28 illustrates the fan angle $\gamma$ of a tilted transaxial fan as in FIG. 27A and FIG. 27B and the corresponding fan angle $\gamma_a$ measured on the xy-plane.

The variation in angular position can be calculated from the detectors in the central row $i_o$. In the absence of the tilt angle $\alpha$, the central row $i_o$ is a transaxial fan and the detector at column j has a fan angle of $\gamma=(j-j_o)*\delta$. When the detector array is tilted at an angle $\alpha$, the fan angle of the detector measured on the transaxial plane is reduced to $\gamma_a$, as illustrated in FIG. 28. It can be seen from FIG. 28 that $$\gamma_a = \gamma * \cos \alpha. \tag{52}$$

Equation 52 indicates that $\gamma_a$ is proportional to $\gamma$, and the angular spacing measured on the transaxial plane between axial fans is still a constant in the tilted detector array. Assuming the angular spacing to be $\delta_a$, Equation 52 gives:

$$(j-j_o)*\delta_a=(j-j_o)*\delta*\cos \alpha,$$

or:

$$\delta_a = \delta * \cos \alpha. \tag{53}$$

Figure 29:
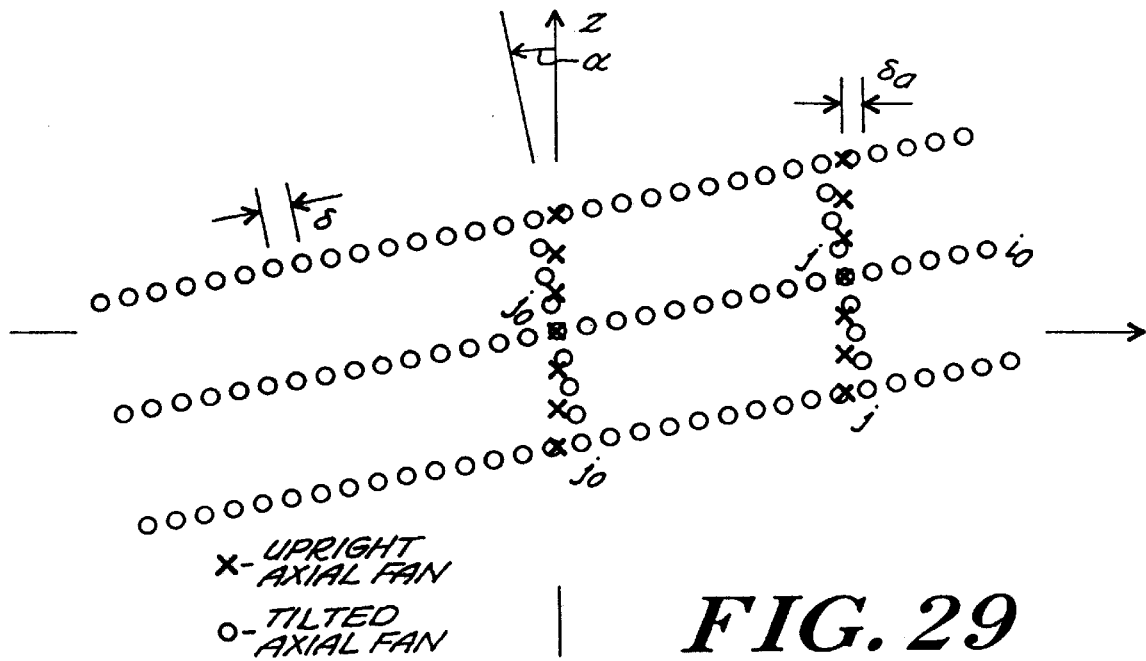
FIG. 29 illustrates the locations of two detector columns which having tilted axial fans and the corresponding locations to be interpolated for generating upright axial fans.

As a result of the tilt angle $\alpha$, the axial fan in each column is tilted by the angle $\alpha$ and therefore is no longer appropriate as a reference for backprojection. However, upright axial fans, that is axial fans parallel to the z-axis, can be interpolated from the tilted projections. The locations of the interpolation points for obtaining an upright axial fan are shown in FIG. 29, where the angular spacing between adjacent axial fans is reduced to $\delta_a$. The central row $i_o$ is the only exception, in that the interpolating points coincide with the detector locations.

Figure 30:
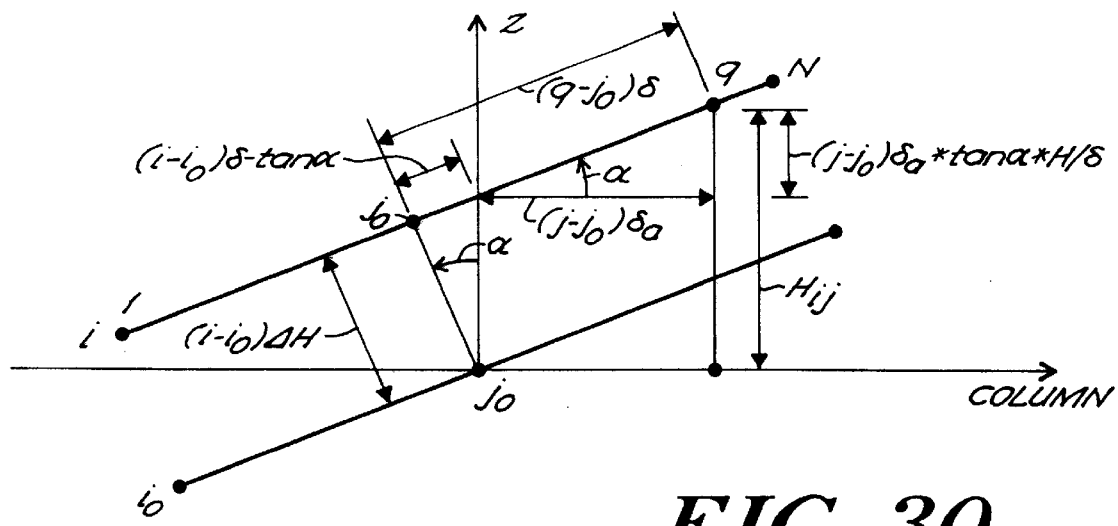
FIG. 30 illustrates the dimensions related to the location at row i and column j of the upright axial fans and the corresponding detector at row i and column q of the titled detector array.

Assuming that the spatial interval between columns is the same as that between rows, in other words, $\delta*R=\Delta H$, the unit $\delta$ in the column dimension is equivalent to the unit $\Delta H$ in the row dimension. The relation between the column number q with tilted axial fans and the column number j with upright axial fans is illustrated in FIG. 30 with:

$$(j-j_o)* \delta_a=(q-j_o)*\delta*\cos \alpha-(i-i_o)*\delta* \sin \alpha. \tag{54}$$

Combining Equations 53 and 54 gives the relationship:

$$q=j+(i-i_o)*\tan \alpha.\text{tm (55)}$$

The z location of the upright axial fan at row i and column j is also shown in FIG. 30 as:

$$H_{ij}=(i-i_o)*\Delta H/\cos \alpha+(j-j_o)*\Delta H*\sin \alpha, \tag{56}$$

where the second term is obtained from $(j-j_o)\delta_a*\tan \alpha*\Delta H*/\delta$ from FIG. 30 and the relation in Equation 53.

Let $$\Delta h_a=\Delta h /\cos \alpha \tag{57}$$

and, applying this to Equations (10) through (13), the z-coordinate of the midpoint $c_{ij}$ becomes $$z_{ij}=(i-i_o)*\Delta h_a*a_j/r+(j-j_o)*\Delta h*\sin \alpha a *a_j/r. \tag{58}$$

Let $Q_{ij}(\theta)$ be the interpolated projection of row i and column j with upright axial fans at the rotation angle of $\theta$. It will be interpolated from the ith row of the collected projections $P_{ij}(\theta)$ at column location of q. Let k be the truncated integer, or remainder, of q and $g_k$ $$q=k+g_k. \tag{59}$$

If linear interpolation is used, interpolated projections $Q_{ij}(\theta)$ can be interpolated from the collected fan-beam projections $P_{ij}(\theta)$ by using Equations 55 and 59 as:

$$Q_{ij}(\theta)=P_{iq}(\theta)=(1.0-g_k)*P_{ik}(\theta)+g_k*P_{i,k+1}(\theta). \tag{60}$$

The interpolated fan-beam projections $Q_{ij}(\theta)$ are analogous to projections $P_{ij}(\theta)$ in the standard geometry except that the spacing between rows and columns becomes $\Delta h$, and $\delta_a$. The z position of $Q_{ij}(\theta)$ is represented by $$z_{ij}(\theta)=z_{ij}+\theta*D/\pi. \tag{61}$$

When $Q_{ij}(\theta)$ is reordered into parallel-beam projections $R_{ij}(\phi)$, like that of $P_{ij}(\theta)$, the z position of $R_{ij}(\phi)$ is represented by:

$$z_{ij}(\phi)=z_{ij}+(\phi-(j-j_o)*\delta_a*D/\pi, \tag{62}$$

which is obtained by replacing $\theta$ with $\phi -(j-j_o)*\delta_a$, in Equation 61. Using Equation 58, the z-position becomes:

$$z_{ij}(\phi)=(i-i_o)*\Delta h_a*a_j/r+(j-j_o)*(\Delta h*\sin \alpha*a_j/r-\delta_a*D/\pi)+\phi*D/\pi. \tag{63}$$

The tilt angle α is preferably chosen to be:

$$\sin \alpha = \delta_a * D/(\Delta h * \pi),$$

which is the same as:

$$\tan \alpha = \delta * D/(\Delta h * \pi). \quad (64)$$

With this tilt angle, the z-position becomes:

$$z_{ij}(\phi)=(i-i_o)*\Delta h_a*a_j/r-(1-a_j/r)*(j-j_o)*\delta_a*D/\pi)+\phi*D/\pi. \quad (65)$$

Equation 65 indicates that near the central column $j_o$, the reordered projections $R_{ij}(\phi)$ are close to a constant z position of:

$$z_{ij0}(\phi)=(i-i_o)*\Delta h_a+\phi*D/\pi.$$

Like the configuration with shifted columns of detectors shown in FIG. 23, it is still preferred to employ constant-z interpolation for achieving accurate results; however the amount of out-of-bounds data is largely reduced at this tilt angle.

Figure 31:
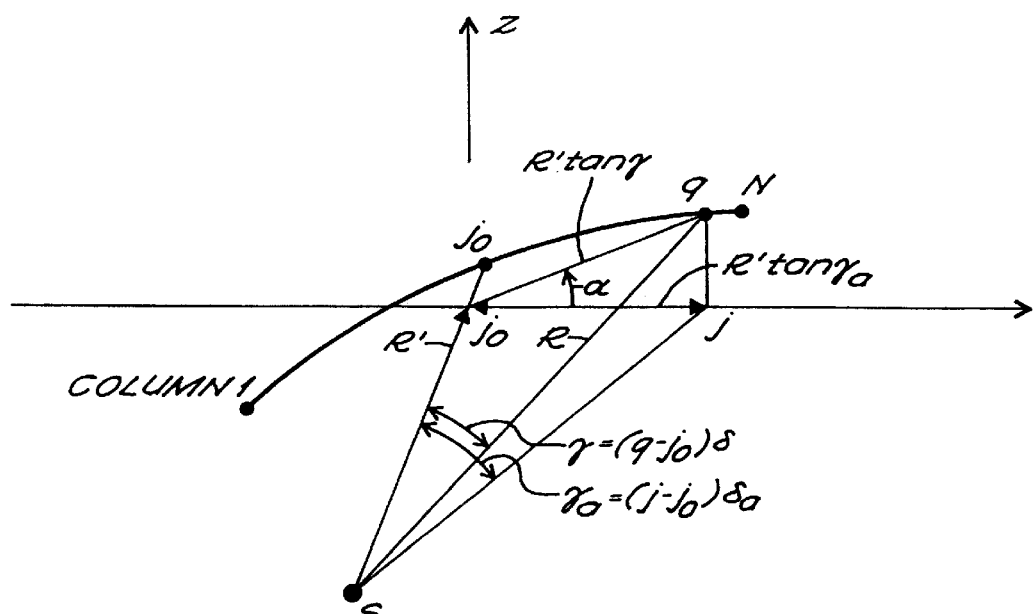
FIG. 31 illustrates the fan angle $\gamma$ of a tilted transaxial fan and the corresponding fan angle $\gamma_a$ measured on the xy-plane by taking account of the circular cylindrical geometry of the detector array.

The above illustrations and derivation of the mathematical equations provide the general geometry of the tilted detector array configuration of FIG. 27A. However, the assumed approximation treats the detector array as a planar array with equal angular spacing between columns. A rigorous and more accurate derivation should take the cylindrical geometry of the detector array into consideration. This is illustrated in FIG. 31 for an transaxial fan tilted by an angle of α. The fan angle γ is reduced to $\gamma_a$ in the transaxial plane with the relation:

$$\tan \gamma_a = \tan \gamma y * \cos \alpha. \quad (66)$$

Figure 32:
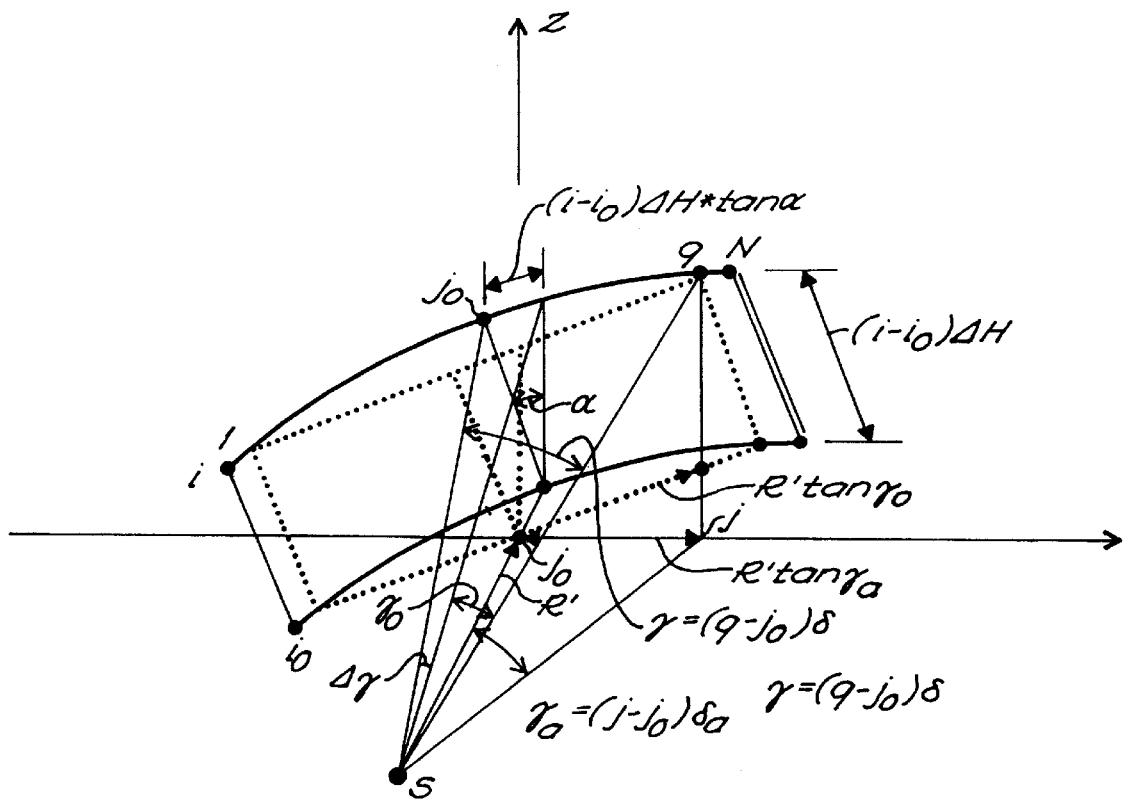
FIG. 32 illustrates the three-dimensional geometry and relation between the upright column j and the detector at row i and column q of a tilted cylindrical detector array.

Comparing this to Equation 52, it can be seen that $\gamma_a$ is no longer proportional to γ, and thus the angular spacing between the titled axial fans is not a constant when it is measured on the transaxial plane. From Equation 66, near the central column $j_o$, where γ is very small and $\gamma_a \approx \gamma * \cos \alpha$, this angular spacing is $$\delta_a = \delta * \cos \alpha \quad (67)$$

as in Equation 53. It is preferable to employ $\delta_a$ as the constant angular spacing for the upright axial fans, which are interpolated from the tilted axial fans. The relation between the column number q of the tilted axial fan and the column number j of the upright axial fan can be derived from FIG. 32, in which:

$$R'*\tan \gamma_a = R'*\tan \gamma_o * \cos \alpha, \text{ with } \gamma_o = \gamma - \Delta\gamma_o.$$

That is:

$$\tan((j-j_o)*\delta_a)=\tan((q-j_o)*\delta-(i-i_o)*\delta*\tan \alpha)*\cos \alpha. \quad (68)$$

From this, the following relationship is obtained:

$$q=j_o+\tan^{-1}(\tan((j-j_o)*\delta a)/\cos \alpha)/\delta+(i-i_o)*\tan \alpha. \quad (69)$$

Based on the number q, $Q_{ij}(\theta)$ can be interpolated from $P_{ij}(\theta)$ as described in Equations 59 and 60.

Figure 33:
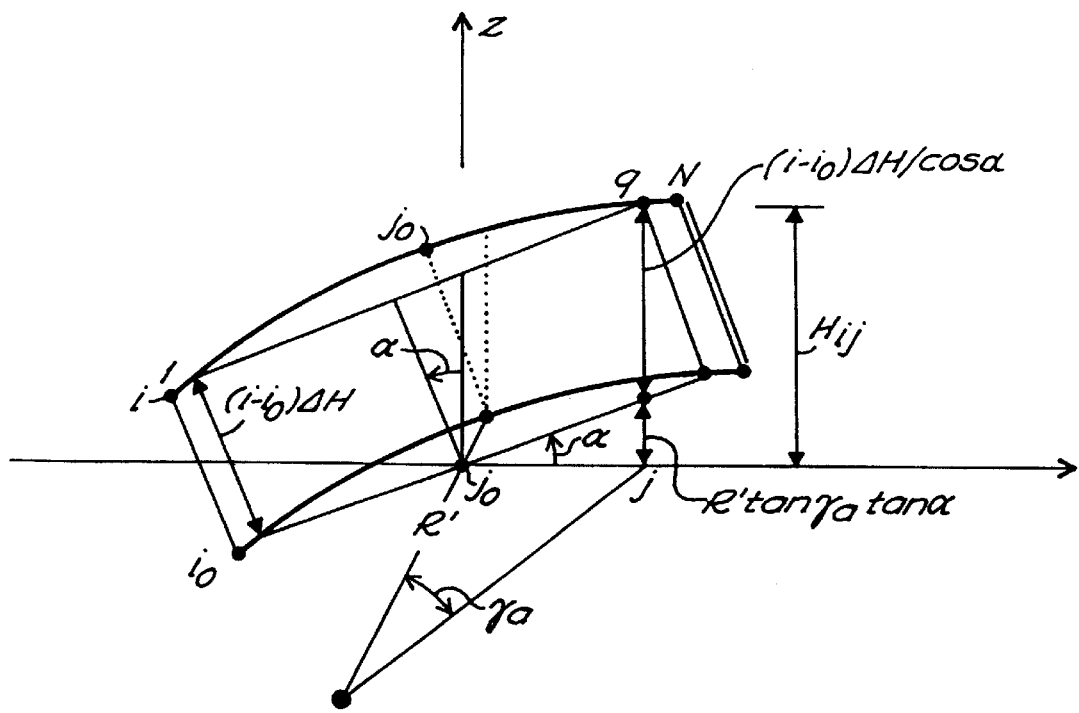
FIG. 33 illustrates the z position of a detector at row i and column q of a tilted cylindrical detector array.

The z location of the upright axial fan at row i and column j is illustrated in FIG. 33:

$$H_{ij}=(i-i_o)*\Delta H/\cos \alpha + R'*\tan \gamma_a * \tan \alpha$$

where $$\gamma_a=(j-j_o)*\delta_a=(j-j_o)*\delta*\cos \alpha.$$

Using $\Delta H = R*\delta$ and the relation $R'/R = \cos \gamma = a_j/r$, gives:

$$H_{ij}=(i-i_o)*\Delta H/\cos \alpha + (j-j_o)*\Delta H * \sin \alpha * (\tan \gamma_a/\gamma_a)*(a_j/r). \quad (70)$$

Equation 70 is the same as Equation 56 except that the factor sin α is modified by $(\tan \gamma_a/\gamma_a)*(a_j/r)$. Therefore, Equation 63 becomes:

$$z_{ij}(\phi)=(i-i_o)*\Delta h_a * a_j/r + (j-j_o)*(\Delta h * \sin \alpha * (\tan \gamma_a/\gamma_a)*(a_j/r)^2 - \delta_a*D/\pi)+\phi*D/\pi; \quad (71)$$

where $\Delta h_a$ is defined in Equation 57.

The tilt angle α is preferably chosen to be:

$$\tan \alpha = \delta * D/(\Delta h * \pi) \quad (72)$$

as in Equation 64. With this tilt angle, the z position becomes:

$$z_{ij}(\phi)=(i-i_o)*\Delta h_a * a_j/r - (1-(\tan\gamma_a/\gamma_a)* (a_j/r)^2)*(j-j_o)*\delta_a*D/\pi)+\phi*D/\pi. \quad (73)$$

Like Equation 65, the reordered projections $R_{ij}(\phi)$ near the central column $j_o$ are close to a constant z-position of:

$$z_{ij0}(\phi)=(i-i_o)*\Delta h_a + \phi*D/\pi.$$

at this tilt angle.

This rigorous technique produces results which are very close to the results achieved using the planar geometry approximation. It is however more complicated to determine the locations q and $z_{ij}(\phi)$ for the reordering and the constant-z interpolations. Whether the approximation or the rigorous technique is used for reconstruction, the above descriptions and illustrations demonstrate that the tilted configuration of FIG. 27A can be used to reconstruct images like the standard geometry with more efficient utilization of detector elements. The tilt angle α is selected according to the pitch of the helical scan, as given by Equation 64 or 72, to minimize the number of out-of-bounds data at this tilt angle.

It is preferable to have the ability to adjust the tilt angle α. A zero tilt angle setting is useful for testing and calibrations, for example. A motor driven mechanism may also be employed, such that the tilt angle can be repositioned to a new setting for every scan, if necessary. With motorized control, it is possible to configure the system for a stationary scan at zero tilt angle. It is also possible to set different tilt angles for different translation speeds. An opposite tilt angle can also be set for reverse helical scan translation.

While this invention has been particularly shown and described with references to preferred embodiments thereof, it will be understood by those skilled in the art that various changes in form and details may be made therein without departing from the spirit and scope of the invention as defined by the appended claims.

For example, although the operation of the improved detector array geometry is described herein in accordance with the constant-z interpolation techniques disclosed herein and disclosed in U.S. patent application Ser. No. 09/038,320, filed Mar. 11, 1998 entitled "Method of and Apparatus for Reconstructing Volumetric Images in a Helical Scanning Computed Tomography System with Multiple Rows of Detectors," by Ching-Ming Lai, incorporated herein by reference, the application of the present invention is not limited to reconstruction techniques which employ constant-z interpolation. The present invention is further applicable to the reconstruction technique of successive approximation described in U.S. application Ser. No. 09/066,494 filed Apr. 24, 1998, entitled "Improved Detector Array Geometry For Helical Scanning Volumetric Computed Tomography System, by Ching-Ming Lai," incorporated herein by reference.

I claim:

1. A computed tomography system for reconstructing a volumetric image of an object including an energy source for irradiating a conical beam centered about a beam axis through the object toward a detector array, said source and said detector array being in rotatable relationship about the object so as to interrogate the object at successive view angles as said object and beam are translated relative to one another along a translation axis normal to the beam axis, wherein the detector array includes an array of sensor elements arranged in rectangular rows and columns positioned in the path of said beam and rotated about the beam axis by a tilt angle $\alpha$, wherein $\alpha \neq 0$, such that said columns lie at the tilt angle $\alpha$ with respect to the translation axis during a scan.

2. The system of claim 1 wherein the tilt angle $\alpha$ is determined as a function of the rate of relative translation of the object and beam.

3. The system of claim 1 wherein the tilt angle $\alpha$ is determined as a function of the rate of rotation of the source and detector array about the object.

4. The system of claim 1 further comprising a mount for mounting the detector array to permit selective adjustment of the tilt angle $\alpha$.

5. The system of claim 4 wherein the mount is motor driven for selecting a range of tilt angles $\alpha$.

6. The system of claim 1 wherein the detector array is planar.

7. The system of claim 1 wherein the detector array is shaped to lie on a cylindrical surface.

8. The system of claim 7 wherein the cylindrical surface is a circular cylindrical surface centered about an axis passing through the source.

9. In a computed tomography system for reconstructing a volumetric image of an object including an energy source for irradiating a conical beam centered about a beam axis through the object toward a detector array, said source and said detector array being in rotatable relationship about the object so as to interrogate the object at successive view angles as said object and beam are translated relative to one another along a translation axis normal to the beam axis, an improved detector array comprising:

a detector array of detector elements arranged in rectangular rows and columns; and a mount for positioning the detector array in the path of said beam at a variable tilt angle $\alpha$ about the beam axis such that said columns lie at the tilt angle $\alpha$ with respect to the translation axis during a scan, wherein $\alpha \neq 0$.

10. The system of claim 9 wherein the tilt angle $\alpha$ is determined as a function of the rate of translation of the object and beam relative to one another.

11. The system of claim 9 wherein the tilt angle $\alpha$ is determined as a function of the rate of rotation of the source and detector array about the object.

12. The system of claim 9 wherein the mount is motor driven for selecting a range of tilt angles $\alpha$.

13. The system of claim 9 wherein the detector array is planar.

14. The system of claim 9 wherein the detector array is shaped to lie on a cylindrical surface.

15. The system of claim 14 wherein the cylindrical surface is a circular cylindrical surface centered about an axis passing through the source.

16. The system of claim 9 wherein the angle $\alpha$ is variable between $-5$ and $+5$ degrees.

17. A detector array for use in a computed tomography system for reconstructing a volumetric image of an object, the system including a source in rotatable relationship with the array about the object for interrogating the object at successive view angles as said object and said source and array are translated relative to one another along a translation axis normal to the plane of rotation; said detector array comprising a two-dimensional array of detector elements arranged in rows and in columns, said detector array being of asymmetric shape with respect to the translation axis.

18. The detector array of claim 17 wherein the detector columns are normal to the detector rows such that the elements are in a rectangular relationship.

19. The detector array of claim 18 wherein the array is of a rectangular shape, and wherein detector elements in the top and bottom detector rows are partially depopulated in opposite corners of the array to provide an array having a substantially helical contour.

20. The detector array of claim 18 wherein the array is of a rectangular shape, and wherein detector elements in the top and bottom detector rows are partially overpopulated in opposite corners of the array to provide an array having a helical contour.

21. The detector array of claim 17 wherein each detector column is shifted along the translation axis by an amount $\Delta Z$ with respect to a central column.

22. The detector array of claim 21 wherein $\Delta Z$ is determined by the system pitch.

23. The detector array of claim 21 wherein $\Delta Z$ is determined by $(j-j_o) * \delta * D * R / (\pi * r)$ where j is the column number, $j_o$ is the central column number, $\delta$ is the angular interval between rows, D is the translation distance during a system rotation angle of $\pi$, R is the radial distance of the detector array from the X-ray source and r is the radial distance of the center of rotation from the X-ray source.

24. The detector array of claim 21 wherein elements of the detector columns are elongated along the translation axis with respect to the elements of a central column.

25. The detector array of claim 24 wherein the detector elements are increasingly elongated as the distance to the central column increases.

26. The detector array of claim 17 wherein the distance between a column and the source decreases gradually as a function of the position of the column with respect to the central column.

27. The detector array of claim 17 wherein the columns and rows of elements of the detector array lie on a cylindrical surface.

28. The detector array of claim 17 wherein the system makes full use of data collected by each element of the detector array.

* * * * *